(12) United States Patent
Sun et al.

(10) Patent No.: US 10,603,328 B2
(45) Date of Patent: Mar. 31, 2020

(54) METHODS OF TREATING ADVANCED PROSTATE CANCER

(71) Applicant: City of Hope, Duarte, CA (US)

(72) Inventors: Zijie Sun, Duarte, CA (US); David Horne, Duarte, CA (US); Junfeng Li, Duarte, CA (US); John E. Shively, Duarte, CA (US); Jun Xie, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 0 days.

(21) Appl. No.: 15/967,442

(22) Filed: Apr. 30, 2018

(65) Prior Publication Data

US 2018/0311261 A1 Nov. 1, 2018

Related U.S. Application Data

(60) Provisional application No. 62/504,331, filed on May 10, 2017, provisional application No. 62/491,421, filed on Apr. 28, 2017.

(51) Int. Cl.
*A61K 31/58* (2006.01)
*A61K 51/04* (2006.01)
*A61P 35/04* (2006.01)

(52) U.S. Cl.
CPC ........... *A61K 31/58* (2013.01); *A61K 51/0493* (2013.01); *A61P 35/04* (2018.01); *A61K 2300/00* (2013.01)

(58) Field of Classification Search
CPC combination set(s) only.
See application file for complete search history.

(56) References Cited

U.S. PATENT DOCUMENTS 5,656,651 A * 8/1997 Sovak ................ A61K 49/0433
514/396
2015/0110814 A1* 4/2015 Olson ................ A61K 31/4166
424/178.1

* cited by examiner

*Primary Examiner* — Robert S Cabral
(74) *Attorney, Agent, or Firm* — Edward D. Grieff; Mintz, Levin, Cohn, Ferris, Glovsky and Popeo, P.C.

(57) ABSTRACT

Provided herein are methods for treating metastatic prostate cancer using anti-androgen compounds and radionuclide-labeled androgens.

35 Claims, 10 Drawing Sheets

FIG. 2A
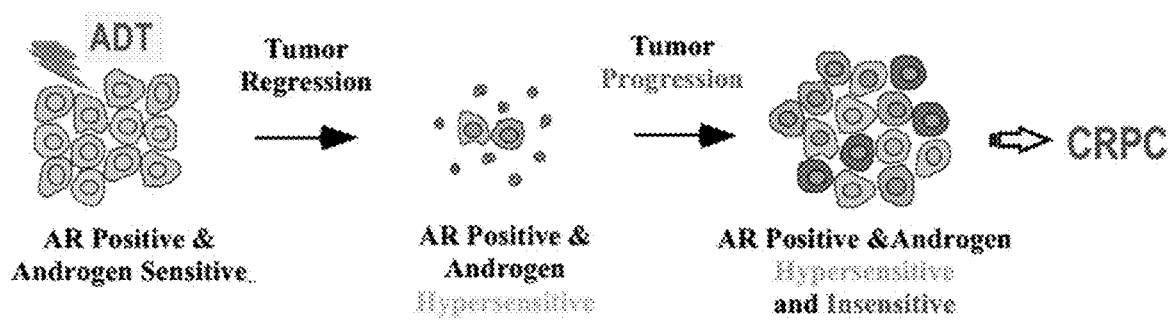
FIG. 2B
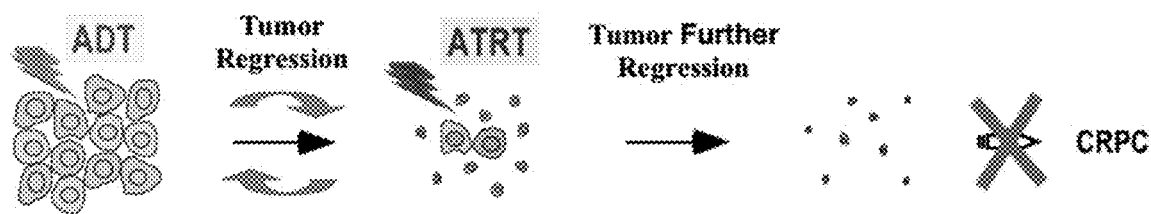
FIG. 3A
| Analog | Docking Score | Prime Energy |
|--------|---------------|--------------|
| DHT    | -13.2         | -10842.6     |
| IVDHT  | -13.5         | -10880.2     |
| IVNDHT | -14.1         | -10884.3     |
| IVMDHT | -14.6         | -10870.9     |

METHODS OF TREATING ADVANCED PROSTATE CANCER

CROSS-REFERENCE TO RELATED APPLICATIONS

This application claims priority to U.S. Application No. 62/504,331 filed May 10, 2017, and U.S. Application No. 62/491,421 filed Apr. 28, 2017, the disclosures of which are incorporated by reference herein in their entirety.

STATEMENT AS TO RIGHTS TO INVENTIONS MADE UNDER FEDERALLY SPONSORED RESEARCH AND DEVELOPMENT

This invention was made with Government support under Grant Numbers R01CA166894, R01CA070297, and R01DK104941 by the National Institutes of Health. The Government has certain rights in the invention.

BACKGROUND

Prostate cancer is the most commonly diagnosed malignancy and the second leading cause of cancer-related death among men in the U.S. Androgen signaling, mediated through the androgen receptor (AR) and its ligands, testosterone and 5α-dihydrotestosterone (DHT), plays a role in prostate tumorigenesis. The AR is a member of the nuclear hormone receptor superfamily. The unbound AR forms a complex with heat-shock proteins (HSPs) in the cytoplasma. Upon binding to ligands, the AR dissociates from the HSPs and translocates into the nucleus, where it binds to the androgen response element (ARE), recruits transcriptional cofactors, and induces transcription. Primary prostate cancer is androgen dependent, and the AR is expressed in prostate cancer cells. Activation of AR mediated through androgens is involved in prostate tumorigenesis, which leads to prostate cancer growth and survival through the activation of targeted gene expression.

Androgen deprivation therapy (ADT) induces significant regression of prostate tumors, which has been a common strategy for treating advanced prostate cancer. However, while ADT initially achieves therapeutic response, it eventually fails in nearly all patients. Consequently, the patients develop castration resistant prostate cancer (CRPC) that is the invariable recurrence of aggressive, lethal prostate cancer in an androgen-depleted setting within two to three years after initiating therapy. Unfortunately, CRPC is incurable to date and almost every patient with metastatic CRPC eventually succumbs to the disease. Despite many different medications that have been developed and applied to patients since then, the fundamental premise behind androgen deprivation has remained almost unchanged. More than 250,000 men die from lethal prostate cancer worldwide each year. Therefore, therapeutic options for the patients are urgently needed. The disclosure is directed to this, as well as other, important ends.

SUMMARY

Provided herein are methods of treating advanced prostate cancer in a subject in need thereof comprising administering to the subject: (i) an effective amount of a compound that reduces the levels of androgens in the subject; and (ii) an effective amount of a radionuclide-labeled androgen; to treat the advanced prostate cancer. In embodiments, the compound that reduces the levels of androgens reduces the levels of testosterone, dihydrotestosterone, or a combination thereof. In embodiments, the compound that reduces the levels of androgens is a small molecule, a peptide, or a protein. In embodiments, the compound that reduces the levels of androgens is a gonadotropin-releasing hormone antagonist or a gonadotropin-releasing hormone agonist. In embodiments, the compound that reduces the levels of androgens is a luteinizing hormone-releasing hormone agonist or a luteinizing hormone-releasing hormone antagonist. In embodiments, the compound that reduces the levels of androgens in the subject is an anti-androgen compound, wherein the anti-androgen compound is abarelix, abiraterone, apalutamide, bicalutamide, degarelix, enzalutamide, flutamide, goserelin, leuprorelin, nilutamide, ozarelix, or a combination of two or more thereof. In embodiments, the radionuclide-labeled androgen is a radionuclide-labeled testosterone, a radionuclide-labeled testosterone analog, a radionuclide-labeled dihydrotestosterone, or a radionuclide-labeled dihydrotestosterone analog. In embodiments, the radionuclide-labeled androgen is a radionuclide-labeled 7α-(E-2'-iodovinyl)-5α-dihydrotestosterone, a radionuclide-labeled 7α-(E-2'-iodovinyl)-17α-methyl-5α-dihydrotestosterone, or a radionuclide-labeled 7α-(E-2'-iodovinyl)-19-nor-5α-dihydrotestosterone. In embodiments, the radionuclide is bismuth$^{-213}$, caesium$^{-131}$, caesium$^{-137}$, chromium$^{-51}$, cobalt$^{-57}$, cobalt$^{-60}$, copper$^{-64}$, copper$^{-67}$, dysprosium$^{-165}$, erbium$^{-169}$, fluorine$^{-18}$, gallium$^{-67}$, gallium$^{-68}$, germanium$^{-68}$, holmium$^{-166}$, indium$^{-111}$, iodine$^{-123}$, iodine$^{-124}$, iodine$^{-125}$, iodine$^{-131}$, iridium$^{-192}$, iron$^{-59}$, krypton$^{-81m}$, lead$^{-212}$, lutetium$^{-177}$, molybdenum$^{-99}$, palladium$^{-103}$, phosphorus$^{-32}$, potassium$^{-42}$, radium$^{-223}$, rhenium$^{-186}$, rhenium$^{-188}$, rubidium$^{-81}$, rubidium$^{-82}$, samarium$^{-153}$, selenium$^{-75}$, sodium$^{-24}$, strontium$^{-82}$, strontium$^{-89}$, technetium$^{-99m}$, thallium$^{-201}$, xenon$^{-133}$, ytterbium$^{-169}$, ytterbium$^{-177}$, or yttrium$^{-90}$. In embodiments, the radionuclide is iodine$^{-125}$, iodine$^{-131}$, or lutetium$^{-177}$. In embodiments, the advanced prostate cancer is metastatic prostate cancer. In embodiments, the advanced prostate cancer is Stage III prostate cancer or Stage IV prostate cancer. In embodiments, the advanced prostate cancer is androgen-sensitive metastatic prostate cancer. In embodiments, the advanced prostate cancer is metastatic castration-sensitive and castration-resistant prostate cancer. In embodiments, the subject has undergone surgical orchiectomy.

Provided herein are methods of treating advanced prostate cancer in a subject in need thereof comprising administering to the subject: (i) an effective amount of an anti-androgen compound; and (ii) an effective amount of a radionuclide-labeled androgen; to treat the advanced prostate cancer. In embodiments, the anti-androgen compound is a gonadotropin-releasing hormone antagonist or a gonadotropin-releasing hormone agonist. In embodiments, the anti-androgen compound is a luteinizing hormone-releasing hormone agonist or a luteinizing hormone-releasing hormone antagonist. In embodiments, the anti-androgen compound is abarelix, abiraterone, apalutamide, bicalutamide, degarelix, enzalutamide, flutamide, goserelin, leuprorelin, nilutamide, ozarelix, or a combination of two or more thereof. In embodiments, the anti-androgen compound is abiraterone, In embodiments, the anti-androgen compound is apalutamide. In embodiments, the anti-androgen compound is bicalutamide. In embodiments, the anti-androgen compound is enzalutamide. In embodiments, the radionuclide-labeled androgen is a radionuclide-labeled testosterone or a radionuclide-labeled testosterone analog. In embodiments, the radionuclide-labeled androgen is a radionuclide-labeled dihydrotestosterone or a radionuclide-labeled dihydrotestosterone analog. In embodiments, the radionuclide-labeled androgen is a radionuclide-labeled 7α-(E-2'-iodovinyl)-5α-dihydrotestosterone, a radionuclide-labeled 7α-(E-2'-iodovinyl)-17α-methyl-5α-dihydrotestosterone, or a radionuclide-labeled 7α-(E-2'-iodovinyl)-19-nor-5α-dihydrotestosterone. In embodiments, the radionuclide is bismuth$^{-213}$, caesium$^{-131}$, caesium$^{-137}$, chromium$^{-51}$, cobalt$^{-57}$, cobalt$^{-60}$, copper$^{-64}$, copper$^{-67}$, dysprosium$^{-165}$, erbium$^{-169}$, fluorine$^{-18}$, gallium$^{-67}$, gallium$^{-68}$, germanium$^{-68}$, holmium$^{-166}$, indium$^{-111}$, iodine$^{-123}$, iodine$^{-124}$, iodine$^{-125}$, iodine$^{-131}$, iridium$^{-192}$, iron$^{-59}$, krypton$^{-81m}$, lead$^{-212}$, lutetium$^{-177}$, molybdenum$^{-99}$, palladium$^{-103}$, phosphorus$^{-32}$, potassium$^{-42}$, radium$^{-223}$, rhenium$^{-186}$, rhenium$^{-188}$, rubidium$^{-81}$, rubidium$^{-82}$, samarium$^{-153}$, selenium$^{-75}$, sodium$^{-24}$, strontium$^{-82}$ strontium$^{-89}$, technetium$^{-99m}$, thallium$^{-201}$, xenon$^{-133}$, ytterbium$^{-169}$, ytterbium$^{-177}$, or yttrium$^{-90}$. In embodiments, the radionuclide is iodine$^{-125}$, iodine$^{-131}$, or lutetium$^{-177}$. In embodiments, the advanced prostate cancer is metastatic prostate cancer. In embodiments, the advanced prostate cancer is Stage III prostate cancer or Stage IV prostate cancer. In embodiments, the advanced prostate cancer is androgen-sensitive metastatic prostate cancer. In embodiments, the advanced prostate cancer is metastatic castration-sensitive and castration-resistant prostate cancer. In embodiments, the subject has undergone surgical orchiectomy.

Provided herein are methods of treating advanced prostate cancer in a subject in need thereof comprising administering to the subject: (i) an effective amount of abiraterone; and (ii) an effective amount of a radionuclide-labeled 7α-(E-2'-iodovinyl)-5α-dihydrotestosterone; wherein the radionuclide is iodine$^{-125}$, iodine$^{-131}$, or lutetium$^{-177}$; to treat the advanced prostate cancer. In embodiments, the radionuclide is iodine$^{-125}$. In embodiments, the radionuclide is iodine$^{-131}$. In embodiments, the radionuclide is lutetium$^{-177}$. In embodiments, the advanced prostate cancer is metastatic prostate cancer. In embodiments, the advanced prostate cancer is Stage III prostate cancer or Stage IV prostate cancer. In embodiments, the advanced prostate cancer is androgen-sensitive metastatic prostate cancer. In embodiments, the advanced prostate cancer is metastatic castration-sensitive and castration-resistant prostate cancer. In embodiments, the subject has undergone surgical orchiectomy.

Provided herein are methods of treating advanced prostate cancer in a subject in need thereof comprising administering to the subject: (i) an effective amount of abiraterone; and (ii) an effective amount of a radionuclide-labeled 7α-(E-2'-iodovinyl)-17α-methyl-5α-dihydrotestosterone; wherein the radionuclide is iodine$^{-125}$, iodine$^{-131}$, or lutetium$^{-177}$; to treat the advanced prostate cancer. In embodiments, the radionculide is iodine$^{-125}$. In embodiments, the radionculide is iodine$^{-131}$. In embodiments, the radionculide is lutetium$^{-177}$. In embodiments, the advanced prostate cancer is metastatic prostate cancer. In embodiments, the advanced prostate cancer is Stage III prostate cancer or Stage IV prostate cancer. In embodiments, the advanced prostate cancer is androgen-sensitive metastatic prostate cancer. In embodiments, the advanced prostate cancer is metastatic castration-sensitive and castration-resistant prostate cancer. In embodiments, the subject has undergone surgical orchiectomy.

Provided herein are methods of treating advanced prostate cancer in a subject in need thereof comprising administering to the subject: (i) an effective amount of abiraterone; and (ii) an effective amount of a radionuclide-labeled 7α-(E-2'-iodovinyl)-19-nor-5α-dihydrotestosterone; wherein the radionuclide is iodine$^{-125}$, iodine$^{-131}$, or lutetium$^{-177}$; to treat the advanced prostate cancer. In embodiments, the radionculide is iodine$^{-125}$. In embodiments, the radionculide is iodine$^{-131}$. In embodiments, the radionculide is lutetium$^{-177}$. In embodiments, the advanced prostate cancer is metastatic prostate cancer. In embodiments, the advanced prostate cancer is Stage III prostate cancer or Stage IV prostate cancer. In embodiments, the advanced prostate cancer is androgen-sensitive metastatic prostate cancer. In embodiments, the advanced prostate cancer is metastatic castration-sensitive and castration-resistant prostate cancer. In embodiments, the subject has undergone surgical orchiectomy.

Provided herein are methods of treating advanced prostate cancer in a subject in need thereof comprising administering to the subject: (i) an effective amount of abiraterone; and (ii) an effective amount of a radionuclide-labeled 7α-(E-2'-iodovinyl)-17α-methyl-5α-dihydrotestosterone; wherein the radionuclide is iodine$^{-131}$; to treat the advanced prostate cancer. In embodiments, the advanced prostate cancer is metastatic prostate cancer. In embodiments, the advanced prostate cancer is Stage III prostate cancer or Stage IV prostate cancer. In embodiments, the advanced prostate cancer is androgen-sensitive metastatic prostate cancer. In embodiments, the advanced prostate cancer is metastatic castration-sensitive and castration-resistant prostate cancer. In embodiments, the subject has undergone surgical orchiectomy.

Provided herein are methods of treating advanced prostate cancer in a subject in need thereof comprising administering to the subject an effective amount of a radionuclide-labeled androgen; wherein the subject has undergone surgical orchiectomy prior to treatment with the radionuclide-labeled androgen; to treat the advanced prostate cancer. In embodiments, the radionuclide-labeled androgen is a radionuclide-labeled testosterone, a radionuclide-labeled dihydrotestosterone, a radionuclide-labeled 7α-(E-2'-iodovinyl)-5α-dihydrotestosterone, a radionuclide-labeled 7α-(E-2'-iodovinyl)-17α-methyl-5α-dihydrotestosterone, or a radionuclide-labeled 7α-(E-2'-iodovinyl)-19-nor-5α-dihydrotestosterone; wherein the radionuclide is iodine$^{-125}$, iodine$^{-131}$, or lutetium$^{-177}$. In embodiments, the radionuclide-labeled androgen is a radionuclide-labeled 7α-(E-2'-iodovinyl)-5α-dihydrotestosterone. In embodiments, the radionuclide-labeled androgen is a radionuclide-labeled 7α-(E-2'-iodovinyl)-17α-methyl-5α-dihydrotestosterone. In embodiments, the radionuclide-labeled androgen is a radionuclide-labeled 7α-(E-2'-iodovinyl)-19-nor-5α-dihydrotestosterone. In embodiments, the radionculide is iodine$^{-125}$. In embodiments, the radionculide is iodine$^{-131}$. In embodiments, the radionculide is lutetium$^{-177}$. In embodiments, the advanced prostate cancer is metastatic prostate cancer. In embodiments, the advanced prostate cancer is Stage III prostate cancer or Stage IV prostate cancer. In embodiments, the advanced prostate cancer is androgen-sensitive metastatic prostate cancer. In embodiments, the advanced prostate cancer is metastatic castration-sensitive and castration-resistant prostate cancer.

BRIEF DESCRIPTION OF THE DRAWINGS

FIG. 1A shows that testosterone (T) is produced in the testes and circulates through the blood with carrier proteins and sex hormone binding globulins (SHBGs), and passively diffuses through the cell membrane. In normal prostate cells, T can be further converted to DHT. The unbound AR forms a complex with heat-shock proteins (HSPs) in the cytoplasm. Upon binding to DHT, the AR dissociates from the HSPs, forms dimers, and translocates into the nucleus, where it binds to the promoters of target genes and activates transcription. FIG. 1B shows that ADT can induce prostate cancer cells to become hypersensitive to androgens through a variety of molecular mechanisms. The hypersensitive tumor cells have high affinity to bind iodine-131-labeled androgen analogs, which leads to DNA damage and cell death.

FIGS. 2A and 2B are diagrams illustrating therapeutic strategies for the treatment of prostate cancer. FIG. 1A shows that current ADT leads to the apoptosis of the majority of prostate cancer cells, but also sensitize tumor cells to induce them to first become androgen hypersensitive or insensitive, which promotes tumor progression and CRPC development. FIG. 1B shows that Applicants new androgen targeted radionuclide therapy (ATRT) can target all AR-positive cells, including the androgen hypersensitive and insensitive cells. Combining ADT and ATRT will produce synergistic therapeutic effects to prevent tumor progression and hormone refractoriness. Cycling the ADT-induced "sensitizing" by ATRT-induced "eliminating" sequence can target and eliminate the potential CRPC "initiating cells" and prevent CRPC development.

FIGS. 3A-3D show the generation of androgen analogs. FIG. 3A shows that docking scores and prime energy scores for DHT and the analogs IVNDHT, IVDHT, and IVMDHT. FIG. 3B shows the docking pose of IVMDHT at AR protein. IVMDHT appropriately fits into the binding pocket of the AR via two hydrogen bonds with R752 and N705 as the DHT molecule. In addition, the vinyl iodine atom of IVMDHT may also form halogen bonds with M780 (3.7 Å), M787 (4.6 Å) and F764 (3.4 Å) based on previous reports. FIG. 3C: The precursor of IVMDHT was labeled with iodine-131. At the final step, labeled IVMDHT products were purified and radiochemical purity was analyzed by HPLC. FIG. 3D: The radiolabeled IVMDHT products were incubated at room temperature for 24 hours and then analyzed with HPLC.

FIGS. 5A-5C: LNCaP cells (AR-positive prostate cancer cell line) were cultured in the absence of androgens for 48 hours after which vehicle only (FIG. 5A panel 1-panel 3) or vehicle with DHT (FIG. 5B panel 1-panel 3) or IVMDHT (FIG. 5C panel 1-panel 3) was added and the cells were incubated for an additional 8 hours. Cells were immunostained with an anti-AR antibody and 4',6-diamidino-2-phenylindole (DAPI) to determine the nuclear location of the AR. FIG. 5D: CV-1 cells were transiently transfected in 48-well plates with 100 ng of luciferase reporter plasmid regulated by 3 androgen response elements (3ARE), 25 ng of pSV40 β-gal, or with or without 20 ng of the human AR expression vector. Twenty-four hours after transfection, 1 or 10 nM DHT, IVMDHT, or vehicle (control) was added to the cells, which were incubated for an additional 24 hours. Then whole cell lysates were prepared to assess luciferase and β-gal activities. Transfection experiments were repeated three times in triplicate. Relative luciferase units (RLUs) were determined from three independent transfections and are presented as the mean+/−SEM. FIG. 5E: Transient infection experiments were repeated in LNCaP cells as described for FIG. 5D but in the absence of human AR expression vectors to assess the activity of DHT and IVMDHT on endogenous AR transcriptional activity.

DETAILED DESCRIPTION

Figure 1A:
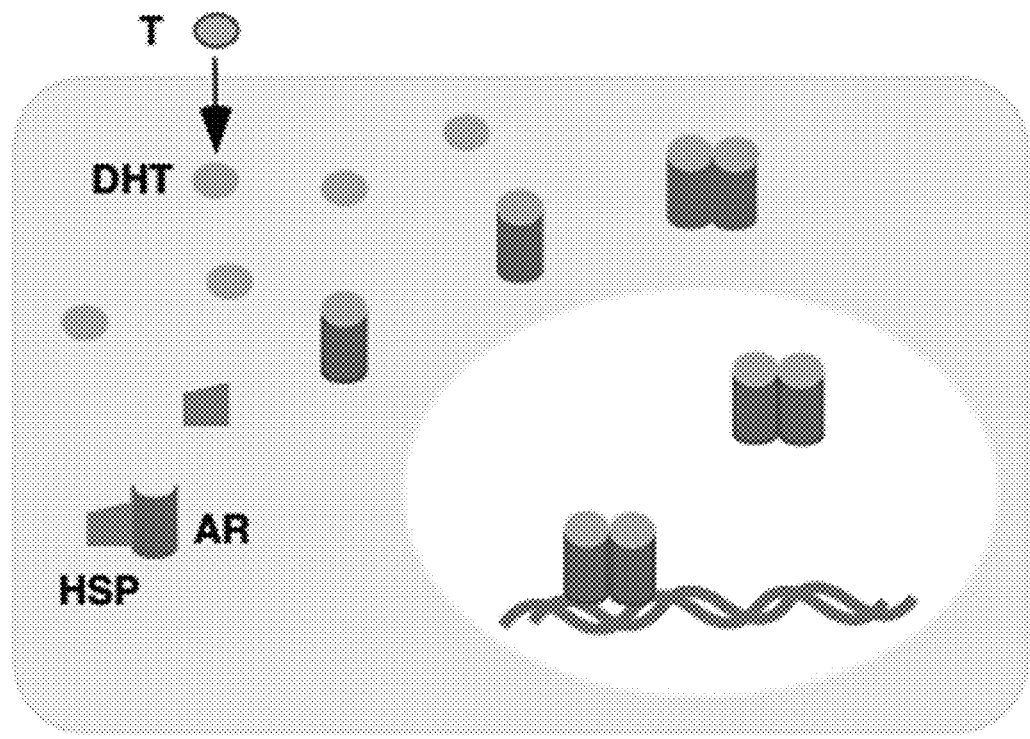
FIGS. 1A and 1B show the molecular mechanism for iodine-131-labeled androgen analogs as radiotherapeutic agents to target androgen-hypersensitive cancer cells.

Androgen receptors are expressed in most, if not all, prostate cancer cells, including those comprising advanced, aggressive, and castration-sensitive and resistant tumors. In addition, current ADT approaches actually sensitize prostate cancer cells and induce them to become hypersensitive to androgens. Capitalizing on these lines of scientific evidence, Applicants provided herein a therapeutic strategy for treating lethal prostate cancer that could prevent or even eliminate castration-resistant prostate cancer (CRPC) development. Central to the originality of this approach is the development and use of novel iodine-labeled (e.g., $^{131}$I) androgen analogs that are structurally similar to the androgen, 5α-dihydrotestosterone (DHT). By exploiting the high affinity of the natural ligand-receptor binding, these analogs will specifically target the AR-expressing tumor cells to cause DNA damage and cell death. Use of these structurally similar analogs to endogenous androgens will provide maximal drug targeting and therapeutic effects, and prevent side effects and drug resistances as observed in other small molecule- and antagonist-based therapies. Most importantly, Applicants will take advantage of the androgen-hypersensitive status of tumor cells and combine this new androgen-targeted radionuclide therapy (ATRT) with current ADT approaches to treat lethal prostate cancer. The idea of combining these two therapies is revolutionary, and could simultaneously produce therapeutic synergy by increasing the specific uptake of radiolabeled androgen analogs by androgen-hypersensitive prostate tumor cells and reduce side effects caused by the standard ADT monotherapies. Moreover, Applicants will use repeated cycles of ADT-induced "sensitization" and ATRT-induced "elimination," which will eliminate the potential CRPC "initiating cells," thus postponing or potentially even preventing CRPC development. In addition, a recent prostate cancer genomic analysis showed that expression of the AR co-exists simultaneously with other genetic and epigenetic changes in both hormone sensitive and insensitive tumor cells during the course of prostate cancer growth and progression. Therefore, this new therapeutic strategy will be able to target almost all prostate cancer cells, including those bearing different AR variants. Because no therapy to date can prevent and eliminate CRPC, this study represents a groundbreaking achievement in the field and provides proof-of-concept for this therapeutic paradigm of using hormone analogs for the treatment of advanced prostate cancers.

Androgen analogs labeled with iodine or other radioactive isotopes can penetrate the cell membrane and bind specifically to the AR both in vitro and in vivo. In addition, many iodine-131 conjugated antibodies and small molecules have proven to be safe and are already frequently used as radio-therapeutic reagents for treating a variety of human malignancies. Emerging evidence indicates that standard ADT sensitizes prostate cancer cells and induces them to become hypersensitive and then insensitive to androgens by aberrantly altering and dysregulating AR signaling pathways. Furthermore, the AR is expressed in almost all prostate cancer cells, including both hormone sensitive and insensitive tumor cells. Given the extremely heterogeneous nature of prostate cancer, directly targeting the AR in prostate cancer cells by using androgen-based radiotherapeutic reagents could provide an elusive, effective therapeutic option for treating lethal prostate cancer.

As described above, given the current challenges to date, the central hypothesis to the methods described herein is that directly targeting the AR in androgen hypersensitive prostate cancer cells through the use of radiolabeled androgen analogs in combination with standard ADT will produce synergistic therapeutic effects and maximize clinical outcomes, ultimately eliminating CRPC.

Although radiolabeled androgen analogs have been developed and used as imaging reagents, they have never been tested and used as radio-therapeutic reagents to directly target androgen-hypersensitive prostate cancer cells in an androgen limited microenvironment in prostate cancer patients during the course of ADT treatment. Applicants have developed and synthesized new androgen analogs that are structurally similar to the natural androgen DHT, and then radionuclide-labeled (e.g., $^{131}$iodine, an FDA-approved radionuclide). Applicants' strategy of using natural androgen analogs to target their natural receptor, AR, a vital molecular marker, through the high affinity of "ligand-receptor" interaction in prostate tumor cells has many advantages for drug delivery and targeting. Given the extremely heterogeneous nature of prostate cancer, directly targeting the AR using androgen-based radiotherapeutic reagents will enable targeting the majority of, if not all, prostate tumor cells and maximize therapeutic effect.

Numerous lines of scientific evidence have shown that ADT sensitizes prostate cancer cells and induces them to become hypersensitive and then insensitive to androgens, which directly contributes to hormone refractoriness, and promotes tumor progression and metastasis. To overcome and exploit this limitation of ADT, Applicants are providing herein a new therapeutic strategy by combining current ADT with androgen-targeted radionuclide therapy (ATRT), which will not only overcome the limitations of ADT but also improve therapeutic responses by increasing the uptake of radiolabeled androgen analogs into androgen-hypersensitive prostate cancer cells.

Although much effort has spent to-date on developing small molecule- and antagonist-based therapies, very limited effort has been given to develop mimics of natural androgens for use as therapeutic agents. The use of structurally similar analogs to natural androgens will provide maximal therapeutic effects and prevent drug resistance that results from physiological responses and circumvention of small molecule-based therapeutics by the body.

Unless defined otherwise, technical and scientific terms used herein have the same meaning as commonly understood by a person of ordinary skill in the art. Any methods, devices and materials similar or equivalent to those described herein can be used in the practice of this invention. The following definitions are provided to facilitate understanding of certain terms used frequently herein and are not meant to limit the scope of the present disclosure.

"TRT" is the abbreviation for targeted radionuclide therapy.

"AR" is the abbreviation for androgen receptor.

"ATRT" is the abbreviation for androgen targeted radionuclide therapy.

"ADT" is the abbreviation for androgen deprivation therapy.

"DHT" is the abbreviation for 5α-dihydrotestosterone.

"IVDHT" is the abbreviation for 7α-(E-2'-iodovinyl)-5α-dihydrotestosterone, which is represented by the structure:

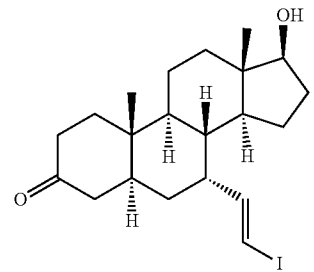

"IVMDHT" is the abbreviation for 7α-(E-2'-iodovinyl)-17α-methyl-5α-dihydrotestosterone, which is represented by the structure:

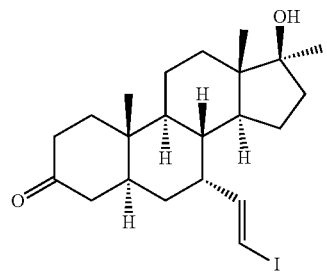

"IVNDHT" is the abbreviation for 7α-(E-2'-iodovinyl)-19-nor-5α-dihydrotestosterone, which is represented by the structure:

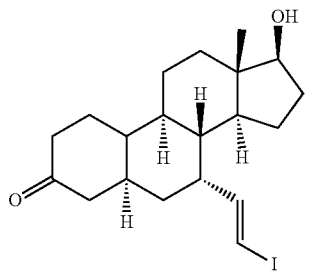

"CRPC" is the abbreviation for castration-resistant prostate cancer.

"Androgen" or "androgen compound" refers to testosterone, dihydrotestosterone, androstenedione, dehydroepiandrosterone, androstenediol, androsterone, and the like. In embodiments, "androgen" refers to testosterone or dihydrotestosterone.

"Anti-androgen compound" refers to any compound that can lower androgen levels in the body. The anti-androgen compounds can be small molecules, peptides, or proteins. In embodiments, the anti-androgen compound refers to a compound used for chemical orchiectomy. In embodiments, the anti-androgen compound is a gonadotropin-releasing hormone (GnRH) antagonist. In embodiments, the anti-androgen compound is a gonadotropin-releasing hormone (GnRH) agonist. In embodiments, the anti-androgen compound is a luteinizing hormone-releasing hormone (LHRH) agonist. In embodiments, the anti-androgen compound is a luteinizing hormone-releasing hormone (LHRH) antagonist. In embodiments, the anti-androgen compound is abarelix, abiraterone, apalutamide, bicalutamide, degarelix, enzalutamide, flutamide, goserelin, leuprorelin (also known as leuprolide), nilutamide, ozarelix, or a combination of two or more thereof. In embodiments the anti-androgen compound is abarelix. In embodiments the anti-androgen compound is abiraterone. In embodiments the anti-androgen compound is apalutamide. In embodiments the anti-androgen compound is bicalutamide. In embodiments the anti-androgen compound is degarelix. In embodiments the anti-androgen compound is enzalutamide. In embodiments the anti-androgen compound is flutamide. In embodiments the anti-androgen compound is goserelin. In embodiments the anti-androgen compound is leuprorelin. In embodiments the anti-androgen compound is nilutamide. In embodiments the anti-androgen compound is ozarelix. In embodiments, the anti-androgen compound is in the form of a pharmaceutically acceptable salt.

"Subject has undergone surgical orchiectomy" refers to a subject that has undergone surgical orchiectomy prior to administration of the radionuclide-labeled androgens described herein. "Surgical orchiectomy" refers to a surgery that removes a subject's testicles.

"Chemical orchiectomy" refers to reducing or eliminating the production of androgens in a subject through the use of an anti-androgen compound. In embodiments, chemical orchiectomy is achieved by administering to a subject a luteinizing hormone-releasing hormone agonist or a luteinizing hormone-releasing hormone antagonist.

"Advanced prostate cancer" refers to and includes metastatic prostate cancer and low-grade prostate cancer that has an increased risk of progression and/or death. In embodiments, advanced prostate cancer is androgen receptor positive. A person skilled in the art could readily diagnose whether a low-grade prostate cancer is an advanced prostate cancer with an increased risk of progression and/or death. See, e.g., Moul, "The Evolving Definition of Advanced Prostate Cancer," Rev. Urol, 6(Suppl. 8):S10-517 (2004).

"Metastatic prostate cancer," which is an advanced prostate cancer, refers to the spread of prostate cancer from the prostate to another adjacent or non-adjacent organ or body part. Cancer occurs at an originating site, e.g., prostate, which site is referred to as a primary tumor, e.g., primary prostate cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if prostate cancer metastasizes to the liver, the secondary tumor at the site of the liver consists of abnormal prostate cells and not abnormal liver cells. The secondary tumor in the liver is referred to a metastatic prostate cancer. Thus, the phrase metastatic prostate cancer refers to a disease in which a subject has or had a primary prostate tumor and has one or more secondary prostate tumors. The term non-metastatic prostate cancer refers to diseases in which subjects have a primary tumor but not one or more secondary tumors.

"Metastatic castration-resistant prostate cancer," which is an advanced prostate cancer, refers to a metastatic prostate cancer that continue to grow even when the amount of testosterone in the body is reduced to low levels. The lowered testosterone levels can be the result of androgen deprivation therapy (e.g., treatment with anti-androgen compounds) or surgical orchiectomy. Generally prostate cancers need normal levels of testosterone to grow; however, castration-resistant prostate cancer can still grow with reduced testosterone levels.

"Stage III prostate cancer," which is an advanced prostate cancer, refers to a metastatic prostate cancer that has grown or metastasized outside the prostate into nearby tissues but has not spread to the lymph nodes or other organs.

"Stage IV prostate cancer," which is an advanced prostate cancer, refers to a metastatic prostate cancer that has spread beyond the prostate into the regional lymph nodes, distant lymph nodes, or other body parts or organs.

"Recurrent prostate cancer" refers to a metastatic prostate cancer that has been detected or returned following initial treatment of a primary prostate cancer with surgery, radiation therapy, or anti-androgen compounds.

"Low-grade prostate cancer" refers to Stage I prostate cancer and Stage II prostate cancer.

The terms or "acceptable," "effective," or "sufficient" when used to describe the selection of any components, ranges, dose forms, etc. disclosed herein intend that the component, range, dose form, etc. is suitable for the disclosed purpose.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and 0-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

"Hormone" generally refers to any member of a class of signaling molecules produced by glands in multicellular organisms that are transported by the circulatory system to target distant organs to regulate physiology and behavior. The term hormone is sometimes extended to include chemicals produced by cells that affect the same cell (autocrine or intracrine signaling) or nearby cells (paracrine signaling). Hormones are used to communicate between organs and tissues for physiological regulation and behavioral activities. Hormones affect distant cells by binding to specific receptors (i.e. hormone receptors) in the target cell resulting in a change in cell function. When a hormone binds to the receptor, it results in the activation of a signal transduction pathway.

The terms "derivative" and "variant" refer to without limitation any compound, which is equally referred to any composition, molecule or composition, which has a structure or sequence derived from the compounds of the present disclosure and whose structure/sequence is sufficiently similar to those disclosed herein.

The term "analog" or "analogs" refer to compounds that have similar structural, physical, chemical, biochemical, and/or pharmacological properties. Certain analogs of a hormone (i.e., an androgen), can share structural similarities with the original hormone and function as an the original hormone.

A "label" is a composition detectable by spectroscopic, photochemical, biochemical, immunochemical, chemical, or other physical means. For example, useful labels include radioisotopes, fluorescent moieties and/or dyes, electron-dense recompositions, enzymes (e.g., as commonly used in an ELISA), biotin, digoxigenin, or haptens and proteins or other entities which can be made detectable, e.g., by incorporating a radioisotope (or radiolabel or radionuclide) into a small molecule, a peptide, or a protein specifically reactive with a target molecule. Any appropriate method known in the art for conjugating a molecule to the label may be employed, e.g., using methods described in Hermanson, Bioconjugate Techniques 1996, Academic Press, Inc., San Diego.

A "labeled molecule" is one that is bound, either covalently, through a linker or a chemical bond, or noncovalently, through ionic, van der Waals, electrostatic, or hydrogen bonds to a label or detectable molecule such that the presence of the labeled molecule may be detected by detecting the presence of the label or used for other purpose such as treatment including killing cancer cells.

A "radionuclide", "radioactive nuclide", "radioisotope", "radioactive isotope", "radioactive compound" or "radiolabel" is an atom that has excess nuclear energy. This excess energy can be either emitted from the nucleus as gamma radiation, or create and emit from the nucleus a new particle (alpha particle or beta particle), or transfer this excess energy to one of its electrons, causing that electron to be ejected as a conversion electron. Radionuclides can be used for their radiation (e.g. irradiation to damage or kill pathogenic cells) or for the combination of chemical properties and their radiation (e.g. tracers and biopharmaceuticals). Some non-limiting examples of radioisotopes include (half-life indicated in parenthesis): bismuth$^{-213}$ (46 min), caesium$^{-131}$ (9.7 d), caesium$^{-137}$ (30 yr), chromium$^{-51}$ (28 d), cobalt$^{-60}$ (5.27 yr), dysprosium$^{-165}$ (2 h), erbium$^{-169}$ (9.4 d), holmium$^{-166}$ (26 h), iodine$^{-123}$ (13 h), iodine$^{-124}$ (4.2 d), iodine$^{-125}$ (60 d), iodine$^{-131}$ (8 d), iridium$^{-192}$ (74 d), iron$^{-59}$ (46 d), lead$^{-212}$ (10.6 h), lutetium$^{-177}$ (6.7 d), molybdenum$^{-99}$ (66 h), palladium$^{-103}$ (17 d), phosphorus$^{-32}$ (14 d), potassium$^{-42}$ (12 h), radium$^{-223}$ (11.4 d), rhenium$^{-186}$ (3.8 d), rhenium$^{-188}$ (17 h), samarium$^{-153}$ (47 h), selenium$^{-75}$ (120 d), sodium$^{-24}$ (15 h), strontium$^{-89}$ (50 d), technetium$^{-99m}$ (6 h), xenon$^{-133}$ (5 d), ytterbium$^{-169}$ (32 d), ytterbium$^{-177}$ (1.9 h), yttrium$^{-90}$ (64 h), cobalt$^{-57}$ (272 d), copper$^{-64}$ (13 h), copper$^{-67}$ (2.6 d), fluorine$^{-18}$ (110 min), gallium$^{-67}$ (78 h), gallium$^{-68}$ (68 min), germanium$^{-68}$ (271 d), indium$^{-111}$ (2.8 d), krypton$^{-81m}$ (13 sec), rubidium$^{-81}$ (4.6 h), rubidium$^{-82}$ (1.26 min), strontium$^{-82}$ (25 d), and thallium$^{-201}$ (73 h). In embodiments, the radioisotope is iodine$^{-125}$, iodine$^{-131}$, or technetium$^{-99m}$. One of more of radioisotopes can be used to a single compound depending on a desired purpose.

The term "target molecule" or "target biomolecule" refers to be any type of non-bio (or synthetic) molecules, biomolecules or biological molecules. For example, the target molecule or biomolecule can be large macromolecules such as proteins or peptides, carbohydrates, lipids, and nucleic acids, as well as small molecules such as hormones and any derivatives thereof that can be found from a living organism or artificially synthesized at least in part.

The term "operable linked", "operably associated", "operably bound", "linked", "associated", "bound", "link(s)", "associate(s)" or "bind(s)" may include covalent and non-covalent linkage, association or bond between at least two components.

The phrase "specifically (or selectively) binds", "binds with (high) specificity" or "binds with (high) affinity", when used with reference to binding or association between two entities (e.g. a specific molecule and its binding partner, in particular, a hormone (or its analog) and a respective receptor thereof), refers to a binding reaction that is determinative of the presence of the specific molecule, often in a heterogeneous population of such and other biologics. Thus, for example, the specified hormone binds to a particular receptor at least two times the background and more typically more than 10 to 100 times background.

A "cancer cell" as used herein refers to a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell" or "cancerous cell" and encompasses cancer cells of a solid tumor, a semi-solid tumor, a primary tumor, a metastatic tumor, and the like. In embodiments, the cancer cell is a prostate cancer cell.

"Treatment," or "therapy" as used herein, covers the treatment of a subject in need thereof, and includes treatment of prostate cancer. "Treating," "treatment" or "therapy" of prostate cancer in subject in need thereof refers to (1) taking steps to obtain beneficial or desired results, including clinical results such as the reduction of symptoms; (2) inhibiting prostate cancer, for example, arresting or reducing the development of prostate cancer or its clinical symptoms; (3) relieving prostate cancer, for example, causing regression of prostate cancer or its clinical symptoms; or (4) delaying the disease. In embodiments, beneficial or desired clinical results include, but are not limited to, reduction and/or elimination of prostate cancer cells.

"Administration," "administering" and the like, when used in connection with a composition refer both to direct administration, which may be administration to cells in vitro, administration to cells in vivo, administration to a subject by a medical professional or by self-administration by the subject and/or to indirect administration, which may be the act of prescribing a composition. When used herein in reference to a cell, refers to introducing a composition to the cell. Typically, an effective amount is administered, which amount can be determined by one of skill in the art. Any method of administration may be used. Compounds (e.g., drugs) may be administered to the cells by, for example, addition of the compounds to the cell culture media or injection in vivo. Administration to a subject can be achieved by, for example, intravenous or intravascular injection, direct intratumoral delivery, and the like.

Administering may mean oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "patient", "subject", or "subject in need thereof" refers to a male mammal suffering from prostate cancer that can be treated by administration of a composition or pharmaceutical composition as provided herein. Non-limiting examples include humans, other mammals, bovines, rats, mice, dogs, monkeys, goat, sheep, cows. In embodiments, a patient is human. The terms "subject" and "patient" may be used herein interchangeably.

According to the methods provided herein, the subject is administered an effective amount of one or more of compositions provided herein to achieve a desired purpose(s). The terms effective amount and effective dosage are used interchangeably. The term effective amount is defined as any amount necessary to produce a desired physiologic response (e.g., inhibition or reduction of tumor growth or killing tumor cells). Effective amounts and schedules for administering the composition can be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100% over a control. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 20th Edition, Gennaro, Editor (2003), and Pickar, Dosage Calculations (1999)).

A "combined synergistic amount" as used herein refers to the sum of a first amount (e.g., an amount of a first androgen deprivation therapy (ADT) composition) and a second amount (e.g., an amount of a cytotoxic hormone receptor binder used in targeted radionuclide therapy (TRT)), and, optionally, a third amount (e.g., an amount of a second ADT composition, which can be identical to or different from the first ADT composition), that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of compounds administered in combination where the measured effect is greater than the sum of the individual effects of each of the compounds administered alone as a single composition.

The term "pharmaceutically acceptable salts" is meant to include salts of the active compounds that are prepared with relatively nontoxic acids or bases, depending on the particular substituents found on the compounds described herein. Thus, the compounds or compositions, which are interchangeably used herewith, of the present disclosure may exist as salts, such as with pharmaceutically acceptable acids. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The terms "cell signaling pathway", "signaling pathway", "cellular signaling" and "signal transduction" interchangeably refers to transmission of a molecular signal in the form of a chemical modification by recruitment of protein complexes along a signaling pathway that ultimately triggers a biochemical event in the cell. Signal transduction occurs when an extracellular signaling molecule activates a specific receptor located on the cell surface or inside the cell. In turn, this receptor triggers a biochemical chain of events inside the cell—known as a signaling cascade—that eventually elicits a response. Depending on the cell, the response alters cell's metabolism, shape, gene expression, or ability to divide. Some examples of signaling pathways concerned in the present disclosure include, but not limited to, androgen (receptor) signaling pathway, AKT pathway, c-MET pathway, NF-kB pathway, Notch signaling pathway, p53 pathway, Ras-Raf-MEK-ERK pathway, STAT signaling pathway, Wnt signaling pathway and YAP/Wnt signaling pathway.

An "anti-hormone" or "anti-hormone composition" is an agent e.g. reagent, compound or molecule) that can antagonize (reduce, lower, negatively affect or inhibit) one or more functions of a hormone that the anti-hormone or the anti-hormone composition targets. Some examples of anti-hormone compositions may include, but are not limited to, hormone analogs, hormone antagonists, and compositions blocking (reducing, lowering, negatively affecting, inhibiting or preventing) the binding/association between the hormone and its receptor(s), i.e. hormone blocking compositions or blockades. In embodiments, "anti-hormone" or "anti-hormone compositions" refers to an anti-androgen compound.

A "cytotoxic hormone receptor binder," as used herein refers to an compound that is capable of binding to a hormone receptor on a cell and killing the cell to expressing the hormone receptor. In embodiment, the cytotoxic hormone receptor is a "radionuclide-labeled hormone receptor binder," which is a cytotoxic hormone receptor binding bound (e.g. covalently bound) to a radionuclide. In embodiments, the cytotoxic hormone receptor binder is a cytotoxic testosterone receptor binder (e.g. a radionuclide-labeled testosterone or radionuclide-labeled testosterone analog). In embodiments, the cytotoxic hormone receptor binder is a radionuclide-labeled androgen (e.g. a radionuclide-labeled androgen or radionuclide-labeled androgen analog).

In one aspect, a method for treating prostate cancer is provided. In embodiments, the method comprises hormone deprivation (or anti-hormone) therapy in combination with a targeted radionuclide therapy, such as a cytotoxic hormone receptor binder. The hormone deprivation (or anti-hormone) therapy induces cancer cells to be sensitive (e.g. hypersensitive) to, or increase prostate cancer cell sensitivity to, a hormone that is targeted by the hormone deprivation therapy. The targeted radionuclide therapy (e.g. follow-on radionuclide therapy), such as a cytotoxic hormone receptor binder, specifically targets and kills the prostate cancer cells, maximizing the efficacy of the treatment. In embodiments, the radionuclide therapy (e.g. follow-on radionuclide therapy), such as a cytotoxic hormone receptor binder, can target and damage the prostate cancer cells with high specificity by delivering radioactive therapeutic or imaging compositions that is labeled to (or associated with) the hormone to which the prostate cancer cells became hypersensitive. In certain embodiments, additional hormone deprivation therapy and/or targeted radionuclide therapy, such as a cytotoxic hormone receptor binder, can be repeatedly administered to the subject to further improve the efficacy of the treatment.

In embodiments, the method is applied to treat a subject suffering from prostate cancer. In embodiments, the method comprises administering a radionuclide-labeled androgen or radionuclide-labeled androgen analog (e.g., radionuclide-labeled dihydrotestosterone or an analog thereof) in combination with androgen deprivation therapy. In embodiments, the radionuclide-labeled androgen is IVDHT, IVMDHT or IVNDHT. In embodiments, the method targets androgen sensitive and/or hypersensitive tumor cells. The methods improve clinical outcomes and reduce and/or prevent CRPC development.

In embodiments, the methods for treating advanced prostate cancer directly target the androgen receptor in prostate cancer cells using radionuclide (e.g. iodine$^{-131}$)-labeled androgen or radionuclide (e.g. iodine$^{-131}$)-labeled androgen analogs as therapeutic compositions. In embodiments, natural androgens or analogs thereof can be used to target their natural androgen receptor (AR), a marker in prostate cancer cell. An androgen deprivation therapy (ADT) can be applied to sensitize prostate cancer cells and induce them to androgen hypersensitive status, directly contributing to tumor progression and hormone refractory. In embodiments, the methods provided herein including combining ADT with androgen targeted radionuclide therapy (ATRT), such as a cytotoxic androgen, overcome the limitation of ADT and improve therapeutic responses by increasing uptake of radiolabeled androgen analogs in tumor cells. In embodiments, the method provides a synergic therapeutic effect. In embodiments, the method reduces clinical side effects caused by monotherapies such as ADT treatment alone. In embodiments, the method provided herein is practiced as a cycle of ADT and ATRT, such as a cytotoxic androgen, in alternating administrations. In embodiments, any part of or an entire cycle of ADT-ATRT can be repeated. Through a plurality of cycles of the "sensitizing" (via ADT) and/or "eliminating" (via ATRT) sequence, CRPC (e.g. initiating) cell development is postponed and/or prevented.

Anti-hormone therapy is a type of hormone deprivation therapy that suppresses selected hormones or their effects. Anti-hormone activity can be achieved by antagonizing hormone function (e.g. with a hormone analog or antagonist, or compositions blocking the binding/association between the hormone and its receptor, (e.g. hormone blocking compositions or blockades)) and/or by preventing or reducing their production. This can be done with drugs, radiation, and/or surgical approaches. The suppression of certain hormones can be beneficial to patients with cancers where certain hormones prompt or help the growth of a tumor. For example, androgen deprivation therapy, using reagents, such as a gonadotropin releasing hormone (GnRH) agonist to reduce endogenous androgen production resulting in low androgen level in body, can be used in treating prostate cancer.

In embodiments, the method provided herein includes administering an androgen deprivation therapy (ADT) to a subject suffering from advanced prostate cancer. Prostate cancer cells typically require androgen hormones, such as testosterone and 5α-dihydrotestosterone (DHT) to grow. In embodiments, ADT can reduce the levels of androgen hormones, with drugs or surgery to prevent the cancer cells from growing or to reduce or diminish the growth of the prostate cancer cells. In embodiments, ADT can decrease the activity of androgen, androgen receptor, the androgen-signaling pathway, or a combination of two or more thereof. The pharmaceutical approaches include, but are not limited to, anti-androgen compounds described herein. In embodiments, similar results can be obtained by surgical orchiectomy.

In embodiments, the disclosure provides methods of treating advanced prostate cancer in a subject in need thereof by administering: (i) an effective amount of a radionuclide-labeled anti-androgen compound, and (ii) a radio-labeled androgen compound, to treat the advanced prostate cancer. In embodiments, the radionuclide-labeled anti-androgen compound includes a radionuclide bound to one of the following: abarelix, abiraterone, apalutamide, bicalutamide, degarelix, enzalutamide, flutamide, goserelin, leuprorelin, nilutamide, or ozarelix. In embodiments, the anti-androgen compound is in the form of a pharmaceutically acceptable salt. Such exemplary pharmaceutically acceptable salts include abiraterone acetate, leuprorelin acetate, and the like. In embodiments, the radionuclide-labeled anti-androgen compound is a radionuclide-labeled abiraterone. In embodiments, the radionuclide-labeled anti-androgen compound is a radionuclide-labeled apalutamide. In embodiments, the radionuclide-labeled anti-androgen compound is a radionuclide-labeled bicalutamide. In embodiments, the radionuclide-labeled anti-androgen compound is a radionuclide-labeled enzalutamide. In embodiments, the radionuclide is bismuth$^{-213}$, caesium$^{-131}$, caesium$^{-137}$, chromium$^{-51}$, cobalt$^{-57}$, cobalt$^{-60}$, copper$^{-64}$, copper$^{-67}$, dysprosium$^{-165}$, erbium$^{-169}$, fluorine$^{-18}$, gallium$^{-67}$, gallium$^{-68}$, germanium$^{-68}$, holmium$^{-166}$, indium$^{-111}$, iodine$^{-123}$, iodine$^{-124}$, iodine$^{-125}$, iodine$^{-131}$, iridium$^{-192}$, iron$^{-59}$, krypton$^{-81m}$, lead$^{-212}$, lutetium$^{-177}$, molybdenum$^{-99}$, palladium$^{-103}$, phosphorus$^{-32}$, potassium$^{-42}$, radium$^{-223}$, rhenium$^{-186}$, rhenium$^{-188}$, rubidium$^{-81}$, rubidium$^{-82}$, samarium$^{-153}$, selenium$^{-75}$, sodium$^{-24}$, strontium$^{-82}$, strontium$^{-89}$, technetium$^{-99m}$, thallium$^{-201}$, xenon$^{-133}$, ytterbium$^{-169}$, ytterbium$^{-177}$, or yttrium$^{-90}$. In embodiments, the radionuclide is iodine$^{-125}$. In embodiments, the radionuclide is iodine$^{-131}$. In embodiments, the radionuclide is lutetium$^{-177}$.

In embodiments, the ADT is a chemical orchiectomy method. Chemical orchiectomy generally reduces the amount of androgens, e.g. testosterone, made by the testicles. Some medicines for chemical orchiectomy, e.g., luteinizing hormone-releasing hormone (LHRH) antagonist and agonist, can lower the amount of testosterone made by the testicles. In embodiments, any therapeutic strategies or compounds that can reduce endogenous androgen production can be used.

In embodiments, ADT utilizes anti-androgen compounds (e.g., such as chemical orchiectomy), surgical orchiectomy, or a combination thereof. In embodiments, ADT uses two or anti-androgen compounds that are administered to a subject simultaneously or separately.

In embodiments, a targeted radionuclide therapy (TRT), such as a cytotoxic hormone receptor binder, can be administered to a subject in need of such treatment. In embodiments, the TRT is radiation therapy. Radiation therapy uses ionizing radiation to kill or diminish cancer cells and shrink tumors, e.g. by damaging the cells' DNA, thereby inhibiting or stopping these cells from continuing to grow and divide. Targeted radionuclide therapy, such as a cytotoxic hormone receptor binder can utilize a molecule labeled with a radionuclide to deliver a cytotoxic level of radiation to disease sites. In targeted radionuclide therapy, such as a cytotoxic hormone receptor binder the biological effect can be obtained by energy absorbed from the radiation emitted by the radionuclide. In embodiments, beta particles, alpha particles, and Auger electrons irradiate tissue volumes with multicellular, cellular and subcellular dimensions, respectively. In embodiments, labels that are mixed emitters can be used to allow both imaging and therapy with the same radionuclide (e.g., the mixed beta/gamma emitter iodine$^{-131}$). Moreover, within each of these categories, there can be multiple radionuclides with a variety of tissue ranges, half-lives, and chemistries, offering various means for tailor-making the properties of a targeted radionuclide therapeutic to the needs of an individual patient.

In embodiments, androgen targeted radionuclide therapy (ATRT), such as a cytotoxic androgen, is administered to a subject suffering from prostate cancer. Therefore, the ATRT, such as a radionuclide-labeled androgen analogs/derivatives that possess the ability of binding to the receptor, is administered to treat prostate cancer. The effect of treating prostate cancer may be, through cytotoxic effects to induce cell death, killing or diminish prostate cancer cells. In embodiments, ATRT, such as a radionuclide-labeled androgen, is administered in combination with androgen deprivation therapy (ADT) to a subject to treat prostate cancer. In embodiments, one or more applications of ATRT, such as a radionuclide-labeled androgen, is administered prior to, substantially simultaneously with or after one or more applications of ADT. In certain embodiments, at least one round (or application) of ATRT, such as a radionuclide-labeled androgen, is administered after the subject is treated with at least one round of ADT. In certain embodiments, ATRT, such as a radionuclide-labeled androgen, is configured to target prostate cancer cells, especially those hypersensitive to androgen via a previously administered ADT. The ATRT, such as a radionuclide-labeled androgen, following the ADT can deliver radiolabeled therapeutic compositions to the androgen-hypersensitive cancer cells by utilizing isotope-labeled androgen or analogs thereof.

In embodiments, androgen targeted radionuclide therapy (ATRT), such as a cytotoxic androgen according to the disclosure, which is labeled with a radionuclide, include a natural androgen or any derivatives thereof. In embodiments, ATRT utilizes any androgen analogs or blockades. Some examples of androgen analogs or blockades that is used in a ATRT include, but not limited, any synthetic androgen analogs or blockades such as (5α,17α,20E)-17β-hydroxy-21-iodopregn-20-en-3-one(17α-((E)-iodovinyl)-5α-DHT), (17α,20E)-17β-hydroxy-21-iodo-7α-methyl-19-norpregna-4,20-dien-3-one(7α-Methyl-17α-((E)-iodovinyl)-19-nortestosterone), 7α-(E-2'-iodovinyl)-19-nor-5α-dihydrotestosterone (IVNDHT), 7α-(E-2'-iodovinyl)-5α-dihydrotestosterone (IVDHT), and 7α-(E-2'-iodovinyl)-17α-methyl-5α-dihydrotestosterone (IVMDHT). In addition, in embodiments, testosterone and dihydrotestosterone, or any derivatives and/or analogs thereof, which possess specific affinity to bind to the AR is used for the above therapeutic purposes. In embodiments, any pharmaceutical compositions used in ADT can also be used in ATRT to be labelled with a radionuclide to target cancer cells. Some examples of such pharmaceutical compositions that can used in ADT as well as in ATRT include, but not limited, abarelix, abiraterone, apalutamide, bicalutamide, degarelix, enzalutamide, flutamide, goserelin, leuprorelin, nilutamide, and ozarelix.

In embodiments, the pharmaceutical compositions used in ATRT is labeled with a radionuclide, e.g. radioactive isotope. Some examples of radionuclides that can have therapeutic functions (e.g. killing or reducing cancer cells) and/or imaging functions (e.g. PET scan), include, but not limited to, bismuth$^{-213}$, caesium$^{-131}$, caesium$^{-137}$, chromium$^{-51}$, cobalt$^{-57}$, cobalt$^{-60}$, copper$^{-64}$, copper$^{-67}$, dysprosium$^{-165}$, erbium$^{-169}$, fluorine$^{-18}$, gallium$^{-67}$, gallium$^{-68}$, germanium$^{-68}$, holmium$^{-166}$, indium$^{-111}$, iodine$^{-123}$, iodine$^{-124}$, iodine$^{-125}$, iodine$^{-131}$, iridium$^{-192}$, iron$^{-59}$, krypton$^{-81m}$, lead$^{-212}$, lutetium$^{-177}$, molybdenum$^{-99}$, palladium$^{-103}$, phosphorus$^{-32}$, potassium$^{-42}$, radium$^{-223}$, rhenium$^{-186}$, rhenium$^{-188}$, rubidium$^{-81}$, rubidium$^{-82}$, samarium$^{-153}$, selenium$^{-75}$, sodium$^{-24}$, strontium$^{-82}$, strontium$^{-89}$, technetium$^{-99m}$, thallium$^{-201}$, xenon$^{-133}$, ytterbium$^{-169}$, ytterbium$^{-177}$, and yttrium$^{-90}$. In embodiments, radionuclides are selected to have a therapeutic function, e.g., killing cancer cells, reducing the number of cancer cells, inhibitor or diminishing the growth of cancer cells, or any combination thereof. In embodiments, the radionuclides are bound to (or associated with or labeled on) the pharmaceutical compositions for ATRT (e.g. androgen analogs) include iodine$^{-124}$, iodine$^{-125}$ or iodine$^{-131}$. In embodiments, one or more of identical or different radionuclides is labeled to a single molecule of ATRT pharmaceutical composition.

In embodiments, the radionuclide-labeled androgen is a radionuclide-labeled testosterone or a radionuclide-labeled testosterone analog. In embodiments, the radionuclide is bismuth$^{-213}$, caesium$^{-131}$, caesium$^{-137}$, chromium$^{-51}$, cobalt$^{-57}$, cobalt$^{-60}$, copper$^{-64}$, copper$^{-67}$, dysprosium$^{-165}$, erbium$^{-169}$, fluorine$^{-18}$, gallium$^{-67}$, gallium$^{-68}$, germanium$^{-68}$, holmium$^{-166}$, indium$^{-111}$, iodine$^{-123}$, iodine$^{-124}$, iodine$^{-125}$, iodine$^{-131}$, iridium$^{-192}$, iron$^{-59}$, krypton$^{-81m}$, lead$^{-212}$, lutetium$^{-177}$, molybdenum$^{-99}$, palladium$^{-103}$, phosphorus$^{-32}$, potassium$^{-42}$, radium$^{-223}$, rhenium$^{-186}$, rhenium$^{-188}$, rubidium$^{-81}$, rubidium$^{-82}$, samarium$^{-153}$, selenium$^{-75}$, sodium$^{-24}$, strontium$^{-82}$, strontium$^{-89}$, technetium$^{-99m}$, thallium$^{-201}$, xenon$^{-133}$, ytterbium$^{-169}$, ytterbium$^{-177}$, or yttrium$^{-90}$.

In embodiments, the radionuclide-labeled androgen is a radionuclide-labeled dihydrotestosterone or a radionuclide-labeled dihydrotestosterone analog. In embodiments, the radionuclide is bismuth$^{-213}$, caesium$^{-131}$, caesium$^{-137}$, chromium$^{-51}$, cobalt$^{-57}$, cobalt$^{-60}$, copper$^{-64}$, copper$^{-67}$, dysprosium$^{-165}$, erbium$^{-169}$, fluorine$^{-18}$, gallium$^{-67}$, gallium$^{-68}$, germanium$^{-68}$, holmium$^{-166}$, indium$^{-111}$, iodine$^{-123}$, iodine$^{-124}$, iodine$^{-125}$, iodine$^{-131}$, iridium$^{-192}$, iron$^{-59}$, krypton$^{-81m}$, lead$^{-212}$, lutetium$^{-177}$, molybdenum$^{-99}$, palladium$^{-103}$, phosphorus$^{-32}$, potassium$^{-42}$, radium$^{-223}$, rhenium$^{-186}$, rhenium$^{-188}$ rubidium$^{-81}$, rubidium$^{-82}$, samarium$^{-153}$, selenium$^{-75}$, sodium$^{-24}$, strontium$^{-82}$, strontium$^{-89}$, technetium$^{-99m}$, thallium$^{-201}$, xenon$^{-133}$, ytterbium$^{-169}$, ytterbium$^{-177}$, or yttrium$^{-90}$.

In embodiments, the radionuclide-labeled androgen is a radionuclide-labeled 7α-(E-2'-iodovinyl)-5α-dihydrotestosterone. In embodiments, the radionuclide is bismuth$^{-213}$, caesium$^{-131}$, caesium$^{-137}$, chromium$^{-51}$, cobalt$^{-57}$, cobalt$^{-60}$, copper$^{-64}$, copper$^{-67}$, dysprosium$^{-165}$, erbium$^{-169}$, fluorine$^{-18}$, gallium$^{-67}$, gallium$^{-68}$, germanium$^{-68}$, holmium$^{-166}$, indium$^{-111}$, iodine$^{-123}$, iodine$^{-124}$, iodine$^{-125}$, iodine$^{-131}$, iridium$^{-192}$, iron$^{-59}$, krypton$^{-81m}$, lead$^{-212}$, lutetium$^{-177}$, molybdenum$^{-99}$, palladium$^{-103}$, phosphorus$^{-32}$, potassium$^{-42}$, radium$^{-223}$, rhenium$^{-186}$, rhenium$^{-188}$, rubidium$^{-81}$, rubidium$^{-82}$, samarium$^{-153}$, selenium$^{-75}$, sodium$^{-24}$, strontium$^{-82}$, strontium$^{-89}$, technetium$^{-99m}$, thallium$^{-201}$, xenon$^{-133}$, ytterbium$^{-169}$, ytterbium$^{-177}$, or yttrium$^{-90}$.

In embodiments, the radionuclide-labeled androgen is a radionuclide-labeled 7α-(E-2'-iodovinyl)-17α-methyl-5α-dihydrotestosterone. In embodiments, the radionuclide is bismuth$^{-213}$, caesium$^{-131}$, caesium$^{-137}$, chromium$^{-51}$, cobalt$^{-57}$, cobalt$^{-60}$, copper$^{-64}$, copper$^{-67}$, dysprosium$^{-165}$, erbium$^{-169}$, fluorine$^{-18}$, gallium$^{-67}$, gallium$^{-68}$, germanium$^{-68}$, holmium$^{-166}$, indium$^{-111}$, iodine$^{-123}$, iodine$^{-124}$, iodine$^{-125}$, iodine$^{-131}$, iridium$^{-192}$, iron$^{-59}$, krypton$^{-81m}$, lead$^{-212}$, lutetium$^{-177}$, molybdenum$^{-99}$, palladium$^{-103}$, phosphorus$^{-32}$, potassium$^{-42}$, radium$^{-223}$, rhenium$^{-186}$, rhenium$^{-188}$, rubidium$^{-81}$, rubidium$^{-82}$, samarium$^{-153}$, selenium$^{-75}$, sodium$^{-24}$, strontium$^{-82}$, strontium$^{-89}$, technetium$^{-99m}$, thallium$^{-201}$, xenon$^{-133}$, ytterbium$^{-169}$, ytterbium$^{-177}$, or yttrium$^{-90}$.

In embodiments, the radionuclide-labeled androgen a radionuclide-labeled 7α-(E-2'-iodovinyl)-19-nor-5α-dihydrotestosterone. In embodiments, the radionuclide is bismuth$^{-213}$, caesium$^{-131}$, caesium$^{-137}$, chromium$^{-51}$, cobalt$^{-57}$, cobalt$^{-60}$, copper$^{-64}$, copper$^{-67}$, dysprosium$^{-165}$, erbium$^{-169}$, fluorine$^{-18}$, gallium$^{-67}$, gallium$^{-68}$, germanium$^{-68}$, holmium$^{-166}$, indium$^{-111}$, iodine$^{-123}$, iodine$^{-124}$, iodine$^{-125}$, iodine$^{-131}$, iridium$^{-192}$, iron$^{-59}$, krypton$^{-81m}$, lead$^{-212}$, lutetium$^{-177}$, molybdenum$^{-99}$, palladium$^{-103}$, phosphorus$^{-32}$, potassium$^{-42}$, radium$^{-223}$, rhenium$^{-186}$, rhenium$^{-188}$, rubidium$^{-81}$, rubidium$^{-82}$, samarium$^{-153}$, selenium$^{-75}$, sodium$^{-24}$, strontium$^{-82}$, strontium$^{-89}$, technetium$^{-99m}$, thallium$^{-201}$, xenon$^{-133}$, ytterbium$^{-169}$, ytterbium$^{-177}$, or yttrium$^{-90}$.

In embodiments, the radionuclide-labeled androgen a radionuclide-labeled 7α-(E-2'-iodovinyl)-19-nor-5α-dihydrotestosterone. In embodiments, the radionuclide is bismuth$^{-213}$, caesium$^{-131}$, caesium$^{-137}$, chromium$^{-51}$, cobalt$^{-57}$, cobalt$^{-60}$, copper$^{-64}$, copper$^{-67}$, dysprosium$^{-165}$, erbium$^{-169}$, fluorine$^{-18}$, gallium$^{-67}$, gallium$^{-68}$, germanium$^{-68}$, holmium$^{-166}$, indium$^{-111}$, iodine$^{-123}$, iodine$^{-124}$, iodine$^{-125}$, iodine$^{-131}$, iridium$^{-192}$, iron$^{-59}$, krypton$^{-81m}$, lead$^{-212}$, lutetium$^{-177}$, molybdenum$^{-99}$, palladium$^{-103}$, phosphorus$^{-32}$, potassium$^{-42}$, radium$^{-223}$, rhenium$^{-186}$, rhenium$^{-188}$, rubidium$^{-81}$, rubidium$^{-82}$, samarium$^{-153}$, selenium$^{-75}$, sodium$^{-24}$, strontium$^{-89}$, strontium$^{-89}$, technetium$^{-99m}$, thallium$^{-201}$, xenon$^{-133}$, ytterbium$^{-169}$, ytterbium$^{-177}$, or yttrium$^{-90}$.

In embodiments, the radionuclide-labeled androgen is a radionuclide-labeled testosterone or a radionuclide-labeled testosterone analog; wherein the radionuclide is iodine$^{-125}$, iodine$^{-131}$, or lutetium$^{-177}$. In embodiments, the radionuclide is iodine$^{-125}$. In embodiments, the radionuclide is iodine$^{-131}$. In embodiments, the radionuclide is lutetium$^{177}$.

In embodiments, the radionuclide-labeled androgen is a radionuclide-labeled dihydrotestosterone or a radionuclide-labeled dihydrotestosterone analog; wherein the radionuclide is iodine$^{-125}$, iodine$^{-131}$, or lutetium$^{-177}$. In embodiments, the radionuclide is iodine$^{-125}$. In embodiments, the radionuclide is iodine$^{-131}$. In embodiments, the radionuclide is lutetium$^{-177}$.

In embodiments, the radionuclide-labeled androgen is a radionuclide-labeled 7α-(E-2'-iodovinyl)-5α-dihydrotestosterone; wherein the radionuclide is iodine$^{-125}$, iodine$^{-131}$, or lutetium$^{-177}$. In embodiments, the radionuclide is iodine$^{-125}$. In embodiments, the radionuclide is iodine$^{-131}$. In embodiments, the radionuclide is lutetium$^{-177}$.

In embodiments, the radionuclide-labeled androgen is a radionuclide-labeled 7α-(E-2'-iodovinyl)-17α-methyl-5α-dihydrotestosterone; wherein the radionuclide is iodine$^{-125}$, iodine$^{-131}$, or lutetium$^{-177}$. In embodiments, the radionuclide is iodine$^{-125}$. In embodiments, the radionuclide is iodine$^{-131}$. In embodiments, the radionuclide is lutetium$^{-177}$.

In embodiments, the radionuclide-labeled androgen a radionuclide-labeled 7α-(E-2'-iodovinyl)-19-nor-5α-dihydrotestosterone; wherein the radionuclide is iodine$^{-125}$, iodine$^{-131}$, or lutetium$^{-177}$. In embodiments, the radionuclide is iodine$^{-125}$. In embodiments, the radionuclide is iodine$^{-131}$. In embodiments, the radionculide is lutetium$^{-177}$.

Labeling a radionuclide to a pharmaceutical composition used in ATRT is done using a wide variety of techniques known in the art. Some examples of such labeling methods can be found at FIGS. 4A and 4B.

In embodiments, the pharmaceutical compositions used for ATRT to target prostate cancer cells comprise androgens or analogs thereof. Therefore, the pharmaceutical compositions used in ATRT can specifically target cells having androgen receptors such prostate cancer cells. In embodiments, ATRT is administered to a subject after the subject is administered with an ADT. The ADT can render the cancer cells hypersensitive to androgens and therefore, upon administration of the pharmaceutical compositions for ATRT (e.g. androgens or analogs thereof which are labeled with radionuclides), the hypersensitive, prostate cancer cells can be more sensitive (or accretive) to the radio-labeled compositions. When the radio-labeled compositions are bound to androgen receptors present on the cancer cells, a cytotoxic level of radiation can be exerted to the cancer cells, resulting in, e.g. DNA damage and cell death. This therapeutic effect by the ATRT can be highly selective and effective, and synergistic to cancer treatment, e.g. prostate cancer, when it is used in combination with ADT. Also, the therapeutic effect by the ATRT can be increased and maximized when it is used in combination with ADT.

The disclosure provides kits an anti-androgen compound and a radionuclide-labeled androgen. In embodiments, the kit includes one or more of radiolabeled-IVDHT, IVMDHT or IVNDHT as a radio-labeled androgen(s). In embodiments, the kit further comprises a document or an instruction that describes a protocol for treating prostate cancer or for administering to a subject in need thereof using an antiandrogen and a radionuclide-labeled androgen.

An effective amount of pharmaceutical compositions used in ADT and TRT is administered to an individual in need thereof. For example, in embodiments, the pharmaceutical compositions for ADT render cancer cells, e.g. prostate cancer cells hypersensitive to androgen, which later leads to inhibiting growth, metastasis and/or invasiveness of cancer cells. In embodiments, the pharmaceutical compositions for TRT has cytotoxic activity, especially to cancer cells, thereby resulting in killing or reducing cancel cells. The amount administered varies depending upon the purpose of administration, the health and physical condition of the individual to be treated, age, the degree of resolution desired, the formulation of the pharmaceutical compositions, the treating clinician's assessment of the medical situation, and other relevant factors. It is expected that the amount will fall in a relatively broad range that is determined through routine trials.

In embodiments, the pharmaceutical compositions for ADT and/or ATRT is administered by infusion or by local injection, e.g. by infusion at a rate of about 10 mg/h to about 200 mg/h, about 50 mg/h to about 400 mg/h, including about 75 mg/h to about 375 mg/h, about 100 mg/h to about 350 mg/h, about 150 mg/h to about 350 mg/h, about 200 mg/h to about 300 mg/h, about 225 mg/h to about 275 mg/h. Exemplary rates of infusion can achieve a desired therapeutic dose of, for example, about 0.5 mg/m$^2$/day to about 10 mg/m$^2$/day, including about 1 mg/m$^2$/day to about 9 mg/m$^2$/day, about 2 mg/m$^2$/day to about 8 mg/m$^2$/day, about 3 mg/m$^2$/day to about 7 mg/m$^2$/day, about 4 mg/m$^2$/day to about 6 mg/m$^2$/day, about 4.5 mg/m$^2$/day to about 5.5 mg/m$^2$/day. Administration (e.g., by infusion) is repeated over a desired period, e.g., repeated over a period of about 1 day to about 5 days or once every several days, for example, about five days, over about 1 month, about 2 months, etc. It also can be administered prior, at the time of, or after other therapeutic interventions, such as surgical intervention to remove cancerous cells. The pharmaceutical compositions for ADT and/or ATRT can also be administered as part of a combination therapy, in which at least one of an immunotherapy, a cancer chemotherapy or a radiation therapy is administered to the subject.

In administering the pharmaceutical compositions for ADT and/or ATRT to a subject, routes of administration (path by which the pharmaceutical compositions for ADT is brought into an individual) may vary. The pharmaceutical compositions can be administered systemically (e.g., by parenteral administration, e.g., by an intravenous route) or locally (e.g., at a local tumor site, by intratumoral administration (e.g., into a solid tumor, into an involved lymph node around primary tumor sites), administration into a blood vessel supplying a solid tumor, etc.)).

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending compositions, solubilizers, thickening compositions, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

In embodiments, ADT and ATRT is administered to a subject in need of prostate cancer treatment. In embodiments, a subject who is in need of prostate cancer treatment is administered with one or more applications of ADT and ATRT in any order. Thus, in embodiments, at least one application of ADT is administered to a subject and later at least one application of ATRT is administered to the subject, i.e. the order of the treatment is ADT+ATRT. In embodiments, at least one application of ATRT is administered to a subject and later at least one application of ADT is administered to the subject, i.e. the order of the treatment is ATRT–ADT. In still embodiments, any additional application of ADT and/or ATRT is administered after ADT or ATRT alone or in combination thereof such as ADT–ATRT or ATRT–ADT treatment. In some preferred embodiments, a subject is administered with ADT first and TRT will be administered after the cancer cells become hypersensitive to androgens via the previous ADT treatment and if desired, additional ADT can follow after the ATRT application, i.e. the order of the treatment is ADT–ATRT–ADT. Further one or more applications of ATRT and/or ADT is added, thereby the order of the treatment is, e.g. ADT–ATRT–ADT–ATRT, ADT–ATRT–ADT–ATRT–ADT, and etc. Each application of ADT and ATRT can span a few minutes to a few months or longer, e.g. about several minutes, about several hours, about one or more days, about one or more weeks, or about one or more months. Also, each application of ADT and ATRT can comprise one or more number of administrations of their pharmaceutical compositions in a certain period. Therefore, for example, a patient is administered five times of anti-androgen compositions for ADT over a period of a month and receive two times of radio-labeled androgen analogs for ATRT over two weeks. Any variations on the dosage of pharmaceutical compositions, treatment period, frequency and repeat of administration in ADT as well as ATRT can be possible and adjusted to meet the desired purpose for each patient.

In embodiments, a time interval before alternating therapies, e.g. administration of TRT after administration of ADT (i.e. ADT–TRT) or vice versa, is adjusted depending on various factors such as the purpose (or desired efficacy) of each therapy and conditions of a patient. For example, when ADT-TRT (with or without any additional therapies can be added after TRT) is applied to a patient, the first administration of ADT is aimed to enhance the androgen sensitivity of cancer cells by about 10%, 20%, 30%, 40%, 50%, 60%, 70%, 80%, 90%, 100%, 200%, 300% or more compared to the cancer cells prior to the administration of ADT. The time interval after the competition of the first ADT and before the initiation of the follow-on TRT is sufficient enough to achieve the desired efficacy, e.g. 50% increase of androgen sensitivity. In embodiments, TRT is aimed to reduce a population (or a number) of cancer cells by at least about 10%, 20%, 30%, 40%, 50%, 60%, 70%, 80%, 90% or 100% compared to the cancer cell population (or number) prior to the administration of TRT. The time interval after the competition of the TRT and before the completion of the treatment or the initiation of any follow-on therapy, e.g. ADT is sufficient enough to achieve the desired efficacy, e.g. 50% reduction of cancer cell population.

In embodiments, the combined effective amount is a combined synergistic amount. As defined above, a "combined synergistic amount" results in a synergistic effect (i.e. an effect greater than an additive effect). Therefore, in embodiments, the effective amount of a pharmaceutical composition(s) for a first therapy, e.g. ADT and the effective amount of a pharmaceutical composition(s) for a second, follow-on therapy, e.g. TRT are a combined synergistic amount.

Embodiments

Embodiment 1. A method of treating a cancer in a subject, the method comprising: administering a hormone deprivation therapy in an amount affective to decrease levels of a hormone or decrease activity of the hormone; and administering an effective amount of a cytotoxic hormone receptor binder wherein the cytotoxic hormone receptor binder is capable of binding to a receptor of the hormone.

Embodiment 2. The method of Embodiment 1, wherein the method further comprises, after the administering the cytotoxic hormone receptor binder, administering the hormone deprivation therapy.

Embodiment 3. The method of any one of Embodiments 1 and 2, wherein the cancer is prostate cancer.

Embodiment 4. The method of any one of Embodiments 1 to 3, wherein the hormone is androgen and the hormone receptor is an androgen receptor.

Embodiment 5. The method of any one of Embodiments 1 to 4, wherein the hormone deprivation therapy is an androgen deprivation therapy.

Embodiment 6. The method of Embodiment 5, wherein the androgen deprivation therapy comprises administering an effective amount of an anti-androgen composition to the subject sufficient to decrease the levels of androgen or decrease the activity of androgen.

Embodiment 7. The method of Embodiment 6, wherein the anti-androgen composition is selected from the group consisting of alfatradiol, abiraterone acetate, aminoglutethimide, apalutamide, bicalutamide, bifluranol, cetrorelix, chlormadinone acetate, cyproterone acetate, degarelix, dienogest, diethylstilbestrol, drospirenone, dutasteride, enzalutamide, epristeride, flutamide, estradiol, estradiol esters, conjugated equine estrogens (e.g., PREMARIN®), ethinylestradiol, finasteride, galeterone, gestonorone caproate, goserelin, histrelin ketoconazole, leuprolide, leuprorelin, medrogestone, medroxyprogesterone acetate, megestrol acetate, nilutamide, nomegestrol acetate, darolutamide, oxendolone, osaterone acetate, progestins, seviteronel, spironolactone, topilutamide, triptorelin and seviteronel.

Embodiment 8. The method of any one of Embodiments 1 to 7, wherein the cytotoxic hormone receptor binder is a radionuclide-labeled hormone receptor binder.

Embodiment 9. The method of any one of Embodiments 1 to 7, wherein the radionuclide-labeled hormone receptor binder is a radionuclide-labeled androgen.

Embodiment 10. The method of Embodiment 9, wherein the anti-androgen composition is selected from the group consisting of alfatradiol, abiraterone acetate, aminoglutethimide, apalutamide, bicalutamide, bifluranol, cetrorelix, chlormadinone acetate, cyproterone acetate, degarelix, dienogest, diethylstilbestrol, drospirenone, dutasteride, enzalutamide, epristeride, flutamide, estradiol, estradiol esters, conjugated equine estrogens (e.g., PREMARIN®), ethinylestradiol, finasteride, galeterone, gestonorone caproate, goserelin, histrelin ketoconazole, leuprolide, leuprorelin, medrogestone, medroxyprogesterone acetate, megestrol acetate, nilutamide, nomegestrol acetate, darolutamide, oxendolone, osaterone acetate, progestins, seviteronel, spironolactone, topilutamide, triptorelin and seviteronel.

Embodiment 11. The method of any one of Embodiments 8-10, wherein the radionuclide-labeled hormone receptor binder comprises a radionuclide selected from the group consisting Bismuth$^{-213}$, Caesium$^{-131}$, Caesium$^{-137}$, Chromium$^{-51}$, Cobalt$^{-57}$, Cobalt$^{-60}$, Copper$^{-64}$, Copper$^{-67}$, Dysprosium$^{-165}$, Erbium$^{-169}$, Fluorine$^{-18}$, Gallium$^{-67}$, Gallium$^{-68}$, Germanium$^{-68}$, Holmium$^{-166}$, Indium$^{-111}$, Iodine$^{-123}$, Iodine$^{-124}$, Iodine$^{-125}$, Iodine$^{-131}$, Iridium$^{-192}$, Iron$^{-59}$, Krypton$^{-81m}$, Lead$^{-212}$, Lutetium$^{-177}$, Molybdenum$^{-99}$, Palladium$^{-103}$, Phosphorus$^{-32}$, Potassium$^{-42}$, Radium$^{-223}$, Rhenium$^{-186}$, Rhenium$^{-188}$, Rubidium$^{-81}$, Rubidium$^{82}$, Samarium$^{-153}$, Selenium$^{-75}$, Sodium$^{-24}$, Strontium$^{-82}$, Strontium$^{-89}$, Technetium$^{-99m}$, Thallium$^{-201}$, Xenon$^{-133}$, Ytterbium$^{-169}$, Ytterbium$^{-177}$, and Yttrium$^{-90}$.

Embodiment 12. The method of any one of Embodiments 9-11, wherein the radionuclide-labeled hormone receptor binder comprises a radionuclide is selected from the group consisting of Iodine$^{-123}$, Iodine$^{-124}$, and Iodine$^{-131}$.

Embodiment 13. The method of Embodiment 1, wherein the cancer is ovarian cancer or breast cancer.

Embodiment 14. The method of Embodiment 13, wherein the hormone is estrogen and the hormone receptor is estrogen receptor.

EXAMPLES

The following examples illustrate certain specific embodiments of the invention and are not meant to limit the scope of the invention.

In some examples, methods that can directly target AR in prostate cancer cells using radiolabel androgen analogs in combining with androgen deprivation therapy in order to achieve maximal therapeutic responses for lethal prostate cancer, and postpone and eliminate CRPC development. For this purpose, a series of experiments are performed to directly target AR in prostate cancer cells using radiolabel androgen analogs. As shown in FIG. 2, ADT can be combined with the androgen targeted radionuclide therapy (ATRT), such as a cytotoxic androgen to maximize therapeutic responses through increasing the specific uptake of iodine$^{-131}$ ($^{131}$I) labeled DHT analogs in prostate cancer cells. Moreover, the ADT-ATRT sequence can be repeated to extend the therapeutic window and increase the synergy and efficacy of these therapies in order to eliminate CRPC initiating cells.

Example 1

Assessing the therapeutic effect of $^{131}$I labeled androgen analogs in preclinical prostate cancer animal models.

Androgen analogs (e.g., IVNDHT) will be tested for their affinity and specificity in binding to their AR in several experimental models. Tissue distributions of these analogs will be assessed. The uptake of these radiolabeled androgen analogs in prostate cancer tissues in both intact and castrated prostate cancer mouse models will be tested. Moreover, the therapeutic effect of the $^{131}$I labeled androgen analogs in the preclinical prostate cancer models will be assessed. In this example four sets of experiments, i.e. Examples 1.1.-1.4, are performed to generate and assess the androgen analogs with high binding affinity in preclinical studies.

Example 1.1

Generating iodinated androgen analogs with high binding affinity with the AR.

Figure 3B:
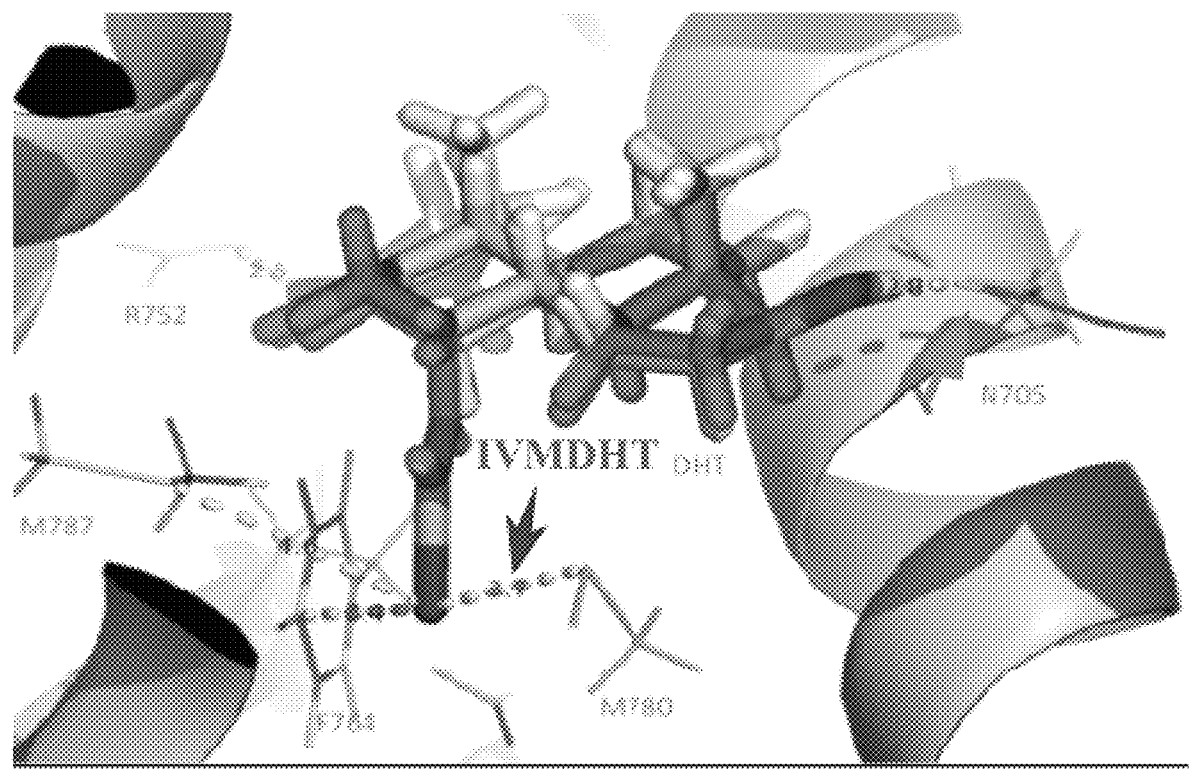
Figure 4A:
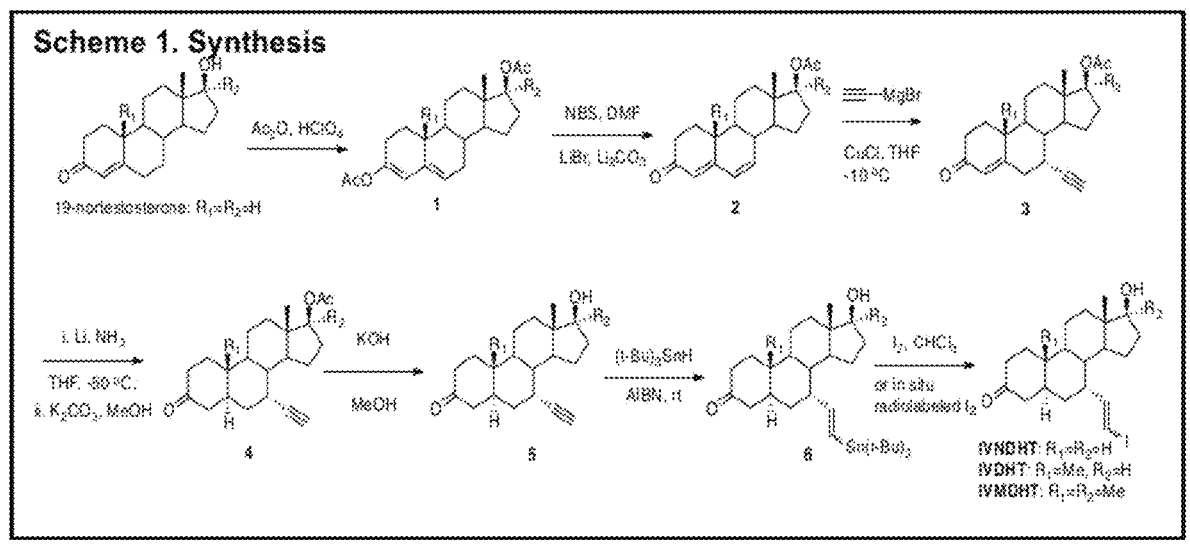
FIGS. 4A-4B show chemical synthetic methods for preparing IVNDHT, IVDHT, and IVMDHT (FIG. 4A) and iodinated bicalutamide (FIG. 4B).

Since the androgen receptor (AR) exhibits higher affinity for dihydrotestosterone (DHT) than for testosterone in prostate cancer cells, iodine$^{-124}$ and iodine$^{-131}$ labeled DHT analogs will be developed using the DHT scaffold as a starting point (FIG. 4A). Previous studies with DHT have shown that substitutions larger than H and F are tolerated at C7 in the a position, this position will be chosen as the point of attachment for incorporating the iodine label. Specifically, an iodovinyl moiety will be used to enhance the ligand's local stability. To prioritize such analogs for synthesis, homology modeling studies (Schrödinger) will be performed by starting with the rat crystal structure (PDBID 1I37) of AR complexed with DHT. Applicant computationally screened more than 30 AR ligands and scored the ligands for lowest energy docking poses. Based on their docking and prime energy scores compared with DHT (FIG. 3A), the following three analogs will be tested: IVNDHT, IVDHT, and IVMDHT. According to the computational results, IVDHT will adopt a similar binding pose to the parent DHT molecule: it resides in the ligand-binding domain of AR and forms two hydrogen bonds with R752 and N705 (FIG. 3B). In addition, the docking studies suggest that incorporating an iodovinyl group (as in IVDHT) improves binding affinity through halogen bonds with M780 (3.7 Å), M787 (4.6 Å) and F764 (3.4 Å). I$^{-124}$ and I$^{-131}$ labeled analogs will be synthesized by techniques known in the field.

FIG. 4A shows a process for synthesizing IVNDHT, IVDHT, and IVMDHT. Commercially available 19-nortestosterone will be treated with acetic anhydride to produce 3,17β-diacetoxy-3,5-estradiene (1). Treatment of compound 1 with NBS followed by acidic workup will afford 17β-acetoxy-4,6-estradien-3-one (2). Grignard reaction of dienone 2 with ethynyl magnesium bromide in the presence of CuCl gives 7α-ethenyl enone 3, which will be added to a Birch solution (prepared by reaction of lithium with liquid ammonium) to produce compound 4. The C17 acetyl group will be hydrolyzed with KOH in methanol and the 7α-ethenyl group of resulting intermediate 5 will be treated with tri-t-butyltin hydride and azobisisobutyronitrile (AIBN) to give the vinyl tri-t-butyltin 6. Quenching of compound 6 with iodine in chloroform will afford non-labeled 7α-iodovinyl compound, IVDHT. To produce IVNDHT labeled with I$^{-124}$ or I$^{-131}$, tin adduct 6 (10-100 μg) will be treated with the radiolabeled iodine composition: 50 μl of a 5% (w/v) solution of NaOAc in glacial AcOH will be combined with [$^{124}$I]NaI or [$^{131}$I]NaI (0.5-2.5 mCi), followed by 100 μl of an oxidant solution consisting of a 2:1 (v/v) mixture of H$_2$O$_2$ (30%) and AcOH. Standard techniques (e.g., solid phase extraction and HPLC) will be used to purify the labeled analog, and its stability will be tested by incubating it at room temperature and 37° C. for 24-48 hours followed by HPLC analysis against a standard. Radiolabeled IVNDHT will be diluted in pH adjusted 1% HSA in PBS buffer for biological analyses. Using a similar overall approach, analog IVDHT will be synthesized by the above route starting with commercially available, 17β-hydroxy-androst-4-en-3-one. Analog IVMDHT will be synthesized as above from commercially available 17β-hydroxy-17α-methyl-androst-4-en-3-one.

In addition to developing these steroidal compositions, small molecule approaches will be adopted to block androgen stimulation of hormone dependent prostate cancer. This class of compounds may be more stable in vivo. To this end, non-steroidal compounds will be developed by labeling small-molecule anti-androgen compounds (FIG. 4B) that are FDA-approved or in late stage clinical trials. Examples of these types of compounds include (1) enzalutamide, an FDA approved diarylthiohydantoin that inhibits translocation of AR to the nucleus, DNA binding, and recruitment of coactivator in metastatic CRPC; (2) apalutamide, a diarylthiohydantoin competitive AR inhibitor that antagonizes AR overexpression; (3) nilutamide, a hydantoin which when combined with orchiectomy enhances progression free survival; (4) flutamide, which synergizes with testicular ablation or chemical suppression for treating prostate cancer by blocking the action of both endogenous and exogenous testosterone, testosterone-stimulated DNA synthesis, and protastic nuclear uptake of androgen; and (5) bicalutamide, a diaryl propionamide compound that is effective as a monotherapy in a subset of patients and (like flutamide) extends time to treatment failure when combined with luteinizing hormone-releasing hormone analogue chemical suppression.

Figure 4B:
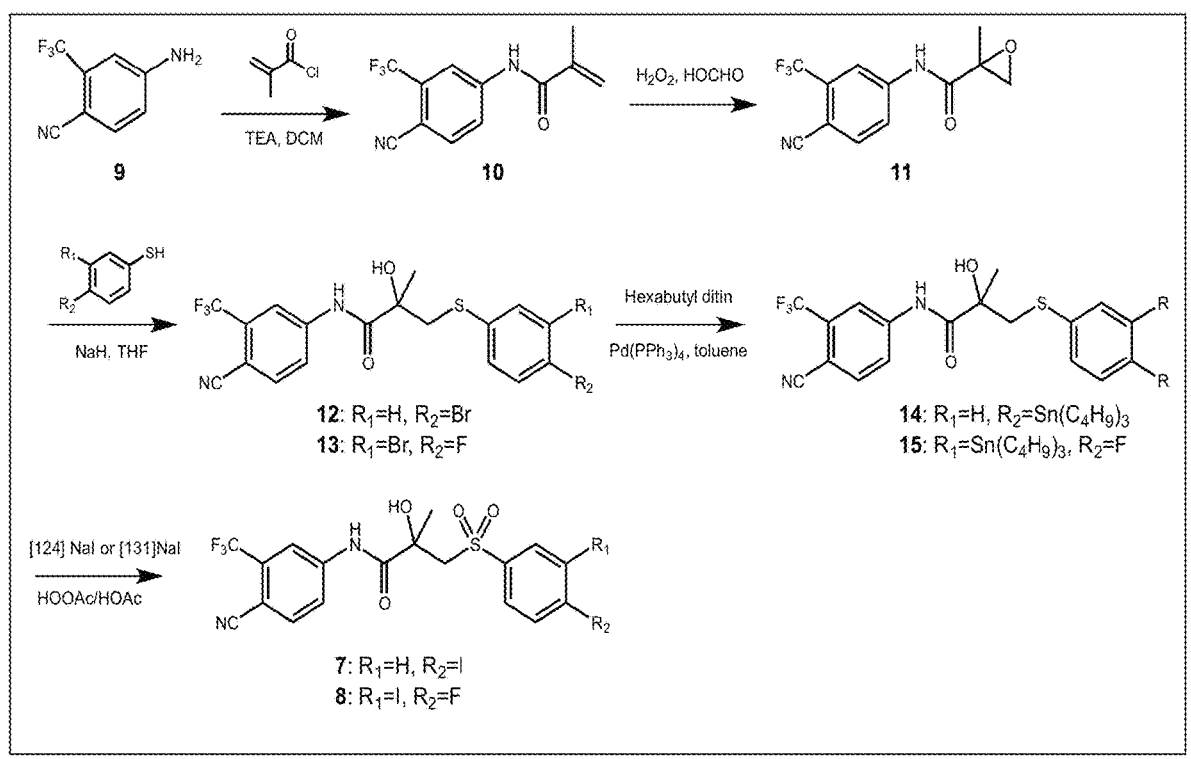

To prioritize syntheses of iodinated analogs of small molecule anti-androgens, homology modeling studies will be performed as described above and the ligands scored for lowest energy docking poses. Based on these results and research into synthetic tractability, two bicalutamide derivatives in which the aromatic ring bearing the sulfonyl group will be labeled with an I$^{-124}$ or I$^{-131}$ have been generated for experimental tests (FIG. 4B). In embodiments, the C19 fluorine has been replaced with an iodine atom as shown in compound 7. In addition, the iodine label has been incorporated to the C19 fluorine as shown in compound 8.

As shown in FIG. 4B, the synthesis of iodinated bicalutamide will be performed by techniques known in the art to incorporate a radiolabel. Briefly, 4-amino-2-(trifluoromethyl)-benzonitrile (9) will be condensed with methacroyl chloride to produce compound 10, which will be treated with performic acid to afford epoxide 11. Opening of the epoxide ring in 11 with either 4-bromothiophenol (R$_1$=H, R$_2$=Br) or 3-bromo-4-fluorothiphenol (R$_1$=Br, R$_2$=F) will give the bromo-thiobicalutamide 12 or 13, respectively, which will be converted to the alkyl tin reagent 14 or 15 using hexabutyl ditin in the presence of tetrakis(triphenylphosphine) palladium(0) catalyst. Labeling of compound 14 or 15 with I-124 or I-131 will be achieved by treatment of these tin adducts with either [124]NaI or [131]NaI in the presence of peracetic acid as described above to produced labeled versions of compound 7 or 8. In embodiments, an alternative strategy of synthesizing iodine-131-labeled anti-androgens will be adopted. Although the binding affinity of non-steroid anti-androgens will appear be lower than that of DHT analogs, they are relatively stable in vivo and have been successfully used as therapeutic agents in prostate cancer patients. Use of iodine-131-labeled anti-androgens would not only competitively inhibit AR binding to endogenous androgens but also induce DNA damage to cause prostate cancer cell death by directly binding to the AR, providing a two-fold therapeutic effect. This will provide another approach for us to develop radiolabeled compounds for TRT in at least some methods of the disclosure.

Example 1.2

Examining the binding affinity between radiolabeled androgen analogs and the androgen receptor in vitro and in vivo.

In this example, microPET imaging and biodistribution assays will be performed using three available and biologically relevant animal models to fully examine the specific binding affinity of IVMDHT with the AR in vivo. In this set of experiments, $^{124}$IVMDHT was generated. 4-month-old castrated and intact C57/B6 male mice (n=4 per group) were tested. $^{124}$IVMDHT was diluted to the appropriate concentration with 0.9% saline/ethanol 9/1 (v/v) prior to injection. All tested mice were given SSKI (saturated solution of potassium iodide) their water bottle 24 hours (20 µg/ml) before they received $^{124}$IVMDHT. Each mouse received an intravenous injection of approximately 0.5 MBq in total 200 µl of $^{124}$IVMDHT into the tail vein under ether anesthesia. Micro PET Images were performed as follows: 0-10 min dynamic scans to determine tissues of immediate uptake and excretion, and 1, 2, 4, 24 and 48 hour scans to determine areas of maximum uptake. At the terminal scan, whole blood and different tissue samples, including liver, lung, kidney, spleen, gut, tumor, testes, prostate, brain, carcass, were taken from both castrated and intact mice. Tissue samples were weighed and counted and the results expressed as % ID/g and total counts per organ. Based on these results (including optimization of dose and specific activity), regions of interested in the terminal scan/biodistribution were calibrated and annotated on the scans to reflect actual ID/g at all time periods. In addition, biodistribution studies will be performed with both castrated and intact mice at 1, 4, 24, and 48 hours (4 mice per time point). The biodistribution results will be analyzed in prostate and other non-AR enrich tissues from intact and castrated mice to determine specific uptake of $^{124}$IVMDHT.

LAPC4 xenograft mice will be used to assess uptake of $^{124}$IVMDHT in human prostate tumor cells. LAPC xenografts will be prepared as described previously. Briefly, 100 µl of LAPC4 cell suspension (1×10$^7$ cells/ml) will be injected subcutaneously into lateral flanks of 6 to 8-week-old athymic male mice. In addition, uptake of $^{124}$IVMDHT will be tested in intact and castrated conditional AR and stabilizing β-catenin transgenic mice, Ctnnb1$^{L(exon3)/+}$/R26hAR$^{L/+}$:PB-Cre, which have been shown to develop AR positive prostatic adenocarcinomas starting at ages around 10-12 weeks. Eight of Ctnnb1$^{L(exon3)/+}$/R26hAR$^{L/+}$:PB-Cre mice from will be castrated at 12-16 weeks after tumor development. After 5 day of orchiectomy, both castrated and intact controls will receive $^{124}$IVMDHT. The similar experimental procedures will be performed as described above for both microPET imaging and biodistribution assays. In the above experiments, the differences of $^{124}$IVMDHT uptake in prostate tumor tissues versus normal tissues, tumor tissues from intact mice versus ones from castrated mice, human xenograft tumor tissues versus mouse prostate tumor tissues will be monitored. Data obtained from the above analyses will provide the critical information regarding the binding affinity of $^{124}$IVMDHT with the human or mouse AR protein and in the absence or presence of androgens. If necessary, both imaging and biodistribution experiments with $^{124}$IVM-DHT will be repeated using rabbit, dog, and monkey models. Finally, as outlined above, both IVDHT and IVMDHT will be tested in the similar experimental settings to identify the best analogs for the clinical study.

Example 1.3

Investigating the therapeutic effect of 131-iodinated androgen analogs in prostate cancer mouse models.

LAPC4 xenograft mice will be used to fully assess the therapeutic effect of $^{131}$IVMDHT in two established and biologically relevant prostate cancer mouse models. Both Ctnnb1$^{L(exon3)/+}$/R26hAR$^{L/+}$:PB-Cre and R26hAR$^{L/+}$:Osr1-Cre mice recapitulate many features of human prostate cancer and mirror the promotional role of androgen signaling in prostate tumorigenesis as seen in humans. Importantly, up-regulation of AR expression has been detected in prostatic tumor cells in those transgenic mice. Laparotomy approaches will be used to identify approximately 20 male Ctnnb1$^{L(exon3)/+}$/R26hAR$^{L/+}$:PB-Cre and R26hAR$^{L/+}$:Osr1-Cre mice with prostate adenocarcinoma formation between the ages of 4-12 months. Ten mice bearing prostatic adenocarcinomas from each of genotypes will receive an intravenous injection of approximately 3.7 MBq in total 200 µl of $^{131}$IVMDHT weekly for 4 consecutive weeks. The rest of 10 mice will be given PBS injections as controls. All mice will be sacrificed and carefully examined at the 8$^{th}$ week after the administration of $^{131}$IVMDHT. The size of the tumors will be measured and the average tumor volumes will be compared and analyzed statistically. The location and size of primary tumors, the extent of local invasion, and the presence of visible metastases in distant organs will be monitored. Given the experimental design, a study with 10 mice per group will have 80% power to detect the difference between treated and control groups, using a two-sided 0.05 alpha level Fisher's exact test. In addition, a series of pathologic and biologic analyses will be performed to evaluate the therapeutic effect by assessing the potential cellular and molecular changes in tumor tissues. Expression of AR, CK8, and E-cadherin will be examined to determine the status of tumor cells. There will be assessment of $^{131}$I generated DNA damage signaling using the anti-gH2AX antibody. In addition, other tissues/organs will also be isolated to evaluate pharmacodynamic effects. Through these analyses, significant information regarding the therapeutic effect of $^{131}$IVMDHT in inhibiting tumor growth for planning a upcoming clinical trial will be generated.

Example 1.4

Assessing the feasibility and efficacy of the new therapeutic strategy by combing the AR-targeted radiotherapies and ADT for the treatment of lethal prostate cancer.

The idea of cycling the ADT initiated "sensitization" and the AR-targeted radiotherapeutics resulted in "elimination" sequence will diminish potential CRPC initiating cells, which eliminates CRPC development. In this example, two sets of experiments will be performed. First, the therapeutic efficacy of $^{131}$IVMDHT will be examined in intact and castrated R26hAR$^{L/+}$:Osr1-Cre mice bearing prostatic adenocarcinomas. The previous study has shown that development of prostatic adenocarcinomas in R26hAR$^{L/+}$:Osr1-Cre transgenic mice relies on the oncogenic role of androgen signaling. Therefore, this relevant mouse model will be used to assess if the depletion of endogenous androgen production increases the specific uptake of $^{131}$IVMDHT in prostatic tumor cells and enhance therapeutic responses. As outlined in Example 1.3, laparotomy approaches will be adopted to identify 60 male R26hAR$^{L/W}$:Osr1-Cre mice with prostate tumor formation between the ages of 10-14 months. 20 mice bearing prostatic adenocarcinomas will be castrated during laparotomy. After 5 days of laparotomy and castration, 10 mice from the castrated or intact group will be given $^{131}$IVMDHT weekly for 4 weeks. The rest of the mice will be given PBS as controls. The treated or untreated but castrated mice will be sacrificed and carefully examined at the 8 weeks week after the laparotomy/castration procedures. The differences in tumor sizes/volumes and pathological changes between those three different groups will be carefully evaluated.

It has been shown that Ctnnb1$^{L(exon3)/+}$/R26hAR$^{L/+}$:PB-Cre develop androgen sensitive prostatic tumors around 2-3 month ages. Both the androgen and Wnt signaling pathways have been demonstrated to play roles in human prostate cancer initiation and progression. Therefore, in the second set of experiments, this relevant mouse model will be used to show that the therapeutic cycle with the ADT initiated "sensitization" and the AR-targeted radiotherapeutics "elimination" will diminish potential CRPC initiating cells. Abiraterone acetate, a specific CYP17 inhibitor that blocks adrenal and intratumoral androgen production, has been used in clinical studies. Given its overall survival benefits as a monotherapy in post-docetaxel CRPC patients, abiraterone acetate will be used. A total of 40 Ctnnb1$^{L(exon3)/+}$/R26hAR$^{L/+}$:PB-Cre mice will be divided into two groups. Group 1 will be administered $^{131}$IVMDHT starting at the 12$^{th}$ week, then repeated at weeks 20 and 28. Group 2 will receive a similar treatment of $^{131}$IVMDHT as Group 1 plus two dosages of abiraterone of 10 mg/kg at weeks 16 and 24. All mice will be sacrificed and carefully examined at week 32. Both gross and pathologic examinations will be done as explained above. In view of the observed effect of the combined therapy, the line of critical information to guide the future clinical study will be determined or adjusted. Alternatively, a few different strategies, including, but not limited to, using prostate conditional Pten knockouts to repeat the above experiments, replacing abiraterone treatment with surgical orchiectomy and androgen pellet insertion, or more androgen analogs will be tested.

Example 2

Assessing the safety and feasibility for prostate cancer patients in using $^{131}$I labeled androgen analogs in a phase I clinical study.

A phase I trial will be performed to translate the bench works to the bedside. With this trial, the safety and feasibility of $^{131}$I labeled androgen analogs in prostate cancer patients in a clinical setting will be directly assessed. Given the differences in androgen metabolism between human and mice, data generated from this example will provide information regarding the specific affinity and biodistribution of androgen analogs in prostate cancer patients.

Both $^{124}$I and $^{131}$I labeled small molecules targeting PSMA have been used in prostate cancer patients for diagnostic and therapeutic purposes. In addition, an androgen analog, 18F-16β-fluoro-5α-dihydrotestosterone (F-FDHT), has been used as an imaging reagent for PET to detect the AR expression in prostate cancer patients undergoing therapy. In this example, a clinical study will directly assess Applicant's strategy using $^{131}$I labeled androgen analogs as therapeutic reagents to directly target the AR positive prostate cancer cells. As detailed in Example 1, a series of preclinical studies will be performed to mirror and mimic human prostate cancer conditions using biologically relevant animal models to test the efficacy of the treatment methods. However, there are some physiologic and biological differences in androgen delivery and metabolism between human and animal models. Specifically, it has been shown that mice do not have sex hormone binding globulin (SHBG) as humans. Therefore, the clinical study will be performed in order to achieve the following goals: (1) determine the safety and feasibility of administration of IVMDHT; (2) evaluate uptake of $^{124}$IVMDHT in prostate cancer tissues in patients with known metastatic adenocarcinoma of the prostate, and (3) investigate if quality of imaging, tumor uptake, normal organ uptake and pharmacokinetics correlate with the presence of hormone sensitive or castration resistant phenotype. Specifically, $^{124}$IVMDHT for PET imaging will be used to assess biodistribution in this study.

Clinical Study Designs:

Patient selection: 18 patients with metastatic prostate cancer will be recruited. All of patients included in this study will be followed up for at least 24 months during the course of the study. Patients will be recruited by the treating medical oncologist or radiation oncologists from patients receiving their prostate cancer treatment. The main Inclusion Criteria will be: (1) men who have histological confirmation of adenocarcinoma of the prostate, (2) evidence of at least one metastasis confirmed by biopsy, (3) metastatic hormone sensitive disease defined as absence of PSA or radiographic progression within 6 months of initiation of androgen deprivation therapy with LHRH agonist or antagonist (cohort 1), and (4) metastatic castration resistant prostate cancer defined by evidence of PSA or radiographic progression despite castrated level of testosterone (<50 ng/dL, cohort 2). Also the following conditions will be used to exclude patients: (1) having concurrent malignancy other than skin cancer, (2) using antiandrogen medications (e.g. bicalutamide, enzalutamide) within 6 weeks of initiation of study imaging, (3) having inability to provide informed consent, and (4) being allergic to iodine. Each patient will provide written informed consent prior to participation in the study.

Radiochemical Synthesis and Preparation of $^{124}$I androgen analogs: As detailed in Example 1.1, $^{124}$IVMDHT will be synthesized. Chemical and radiochemical quality assurance (QA) will be assessed by radiothin-layer chromatography and reversed phase high-performance liquid chromatography (HPLC) through elution with a fully characterized nonradioactive standard. Other important QA will include, e.g., confirmation of color, appearance, radioactive half-life, pH, sterility, endotoxin, and immunoreactivity. The investigators will ensure all QA results being in full accordance with the approved specifications for the best outcomes for patients. The standard for the radiochemical purity in this study can be greater than 99%, which has been achieved in the pilot experiments with $^{131}$IVMDHT. Based on the preliminary data, the final radiolabeled analogs can be formulated in a 1% ethanol solution, packaged in identical 5 mL glass vials, and precluding the use of a bolus injection because of the burning sensation at the injection site associated with the intravenous administration of alcohol. An on-site Q/C test will be performed prior to androgen analog administration using an ITLC procedure if necessary.

Dosimetry imaging and pharmacokinetics of $^{124}$I androgen analogs: following signing informed consent and appropriate screening, all eligible patients will receive approximately 300 mg of potassium iodide orally, in three doses daily during 2 days, to block thyroid uptake of free radioactive iodide. Activity, volume, date and time of the radiopharmaceutical androgen analogs will be recorded on the CRF. Injections will be manually performed using a lead-shielded syringe. $^{124}$IVMDHT will be added to approximately 10 mL of saline with 1% human serum albumin (HSA) and mixed prior to infusion. Each patient will receive an intravenous injection of approximately 180-200 MBq of $^{124}$IVMDHT in the arm. Administration begins with the intravenous administration of a 500 µl test dose. If no adverse reactions are observed after 15 minutes, then the remainder of the dose will be administered intravenously by syringe pump at a rate of 2 ml/minute. After the injection is completed, the patients will be then observed per routine protocol. The remaining activity in the vial and the syringe will be measured with a dose calibrator and recorded in the CRF. In addition to routine observation, vital signs including pulse, blood pressure, and temperature will be taken prior to study drug administration, every 15 minutes for up to one hour following administration, and at each imaging time point.

PET/CT image acquisition: the PET-CT examinations will be analyzed and interpreted. Serial PET/CT images will be obtained approximately 1 hour post-administration and again at approximately 4, 24, 48 and 72 hours. PET images will be performed in 3D mode (septa retracted) and corrected for tissue attenuation based on co-registered CT acquired during the same examination. The following parameters will be used in the scans: slice thickness of 5 mm; increments of 0.8 mm; soft tissue reconstruction kernel; 130 keV and 80 mAs. Immediately after CT scanning, a whole body PET will be acquired in 3D mode from head to toe in two serial acquisitions at the initial time point and head to mid-thigh at subsequent time points. Only head to mid-thigh acquisitions will be obtained at the initial time point. PET images will be reconstructed with spatial resolution of approximately 9 mm full-width-at-half maximum (FWHM) using an iterative algorithm (OSEM). The I$^{-124}$ SUVs will be evaluated in tumors, adjacent non-tumor tissue and selected non-tumor organs and tissues (heart, extracardiac mediastinum, liver, skeletal muscle). Tumor sizes, if applicable depending on site of metastases will be estimated from co-registered CT. Tumor uptake of $^{124}$IVMDHT will be parameterized in terms of single-voxel maximum values SUVmax and whole-tumor volumes of interest (SUVwhtum) as defined from the co-registered CT images. Ratios of tumor to non-tumor activity concentration will also be calculated for adjacent tissue, extracardiac mediastinum, liver, and skeletal muscle. Receiver-operator curve (ROC) analysis will be performed to estimate optimal cutoff values of SUVmax, SUVwhtum, tumor:background and tumor: organ ratios for classifying tumors as "positive" or "negative." Calibration of the PET activity will be performed by imaging a volume of $^{124}$IVMDHT measured in an ISOMFD 1010 dose calibrator to develop a calibration factor that allows for correction of prompt gamma emissions and the low positron fraction of $^{124}$I. The activity of a 10 mL imaging standard containing a minimal amount of $^{124}$IVMDHT will be measured in advance of each PET/CT scan in the dose calibrator and a performer (or investigator or clinician) will set this syringe adjacent to the head of the patient during the scan.

Image quantification: volumes of interest (VOIs) will be created from the sum of adjacent transaxial regions of interest (ROIs) manually drawn along the boundaries of a standard set of normal organs and tissues, using CT as a guide, including salivary glands, brain, heart, kidneys, liver, lungs, spleen, thyroid, muscle, abdomen, tumor lesions and whole body. VOIs will be created on the 4 h time point and copied to all other time points for each patient and repositioned if needed using the fused CT for proper placement. Count activity for each volume will be extracted using a commercially available nuclear medicine workstation. Initial whole body count activity from head and mid-thigh will be summed with the mid-thigh to toe counts to determine total body uptake immediately post-injection (1 h p.i. and prior to voiding) and considered to be equal to 100% of the injected activity of $^{124}$IVMDHT. All organs (and whole body) VOI data will be divided by the initial total body VOI value to obtain the fractional amount of injected activity in each VOI/organ and corrected for radioactive decay of $^{124}$I to the time of injection. The resulting decay corrected estimates of factional activity distribution will be used in the biomodeling.

Radiometabolite Analysis of $^{124}$I androgen analogs: Patients who undergo the above scans will have blood samples drawn to determine the clearance of $^{124}$IVMDHT and the rate of metabolite formation. Blood samples will be taken before the injection of $^{124}$IVMDHT and following each scan time points at 1, 4, 24, 48, and 72 hours. The activities in whole blood, plasma, 30-kDa filtered plasma, and acetonitrile-precipitated plasma will be routinely determined. In addition, the relative amounts of $^{124}$IVMDHT metabolites in the plasma will be determined by HPLC. In addition, 1241 activity in all samples will also be assayed in a γ-counter calibrated for $^{124}$I, corrected for decay to the time of injection, and expressed as a percentage of the injected dose per gram. In addition, levels of total and free androgens will be assessed in each of patient samples.

Absorbed dose calculations: In this study, the absorbed doses of $^{124}$IVMDHT in prostate tumor tissues will be closely monitored. The OLINDA/EXM software will be used in this study. The above software contains a complete series of dosimetry phantoms corresponding to different ages in human tissues/organs and the adult male dosimetry phantom will be used exclusively for computing all absorbed dose estimates. The urinary bladder will be assumed to void regularly at 4.8 h intervals and the gut transit times of the human adult male were assumed. Kidney absorbed doses will be calculated using the adult male phantom's default kidney mass. The calculation of absorbed dose to salivary glands will be performed using spherical S-values, which is the absorbed dose per unit cumulated activity and varies inversely with mass.

Example 3

Figure 5A:
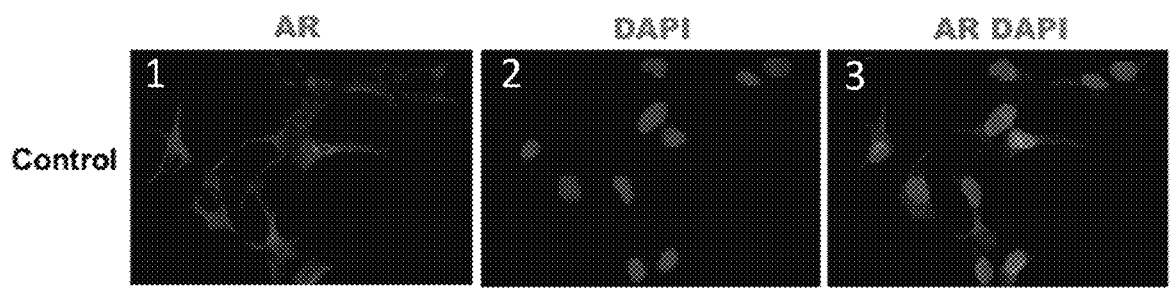
FIGS. 5A-5E shows that IVMDHT, an androgen analog, have similar bioactivity to DHT.
Figure 5B:
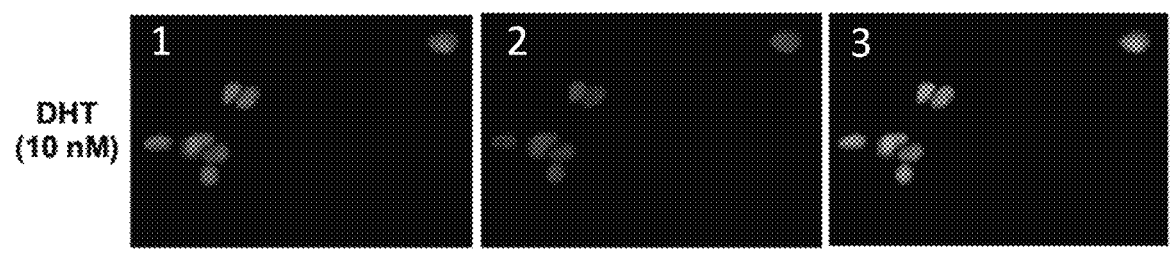
Figure 5C:
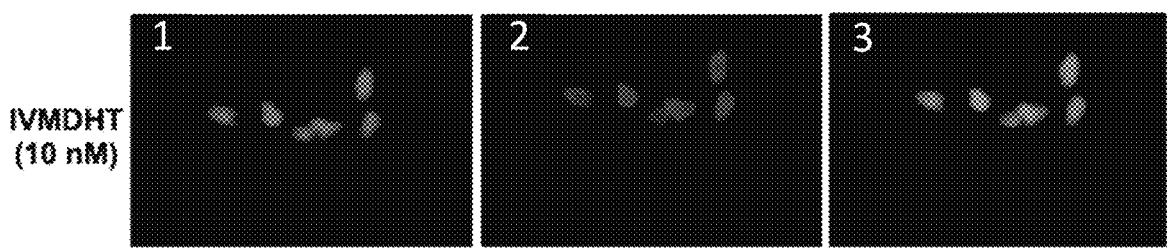
Figure 5D:
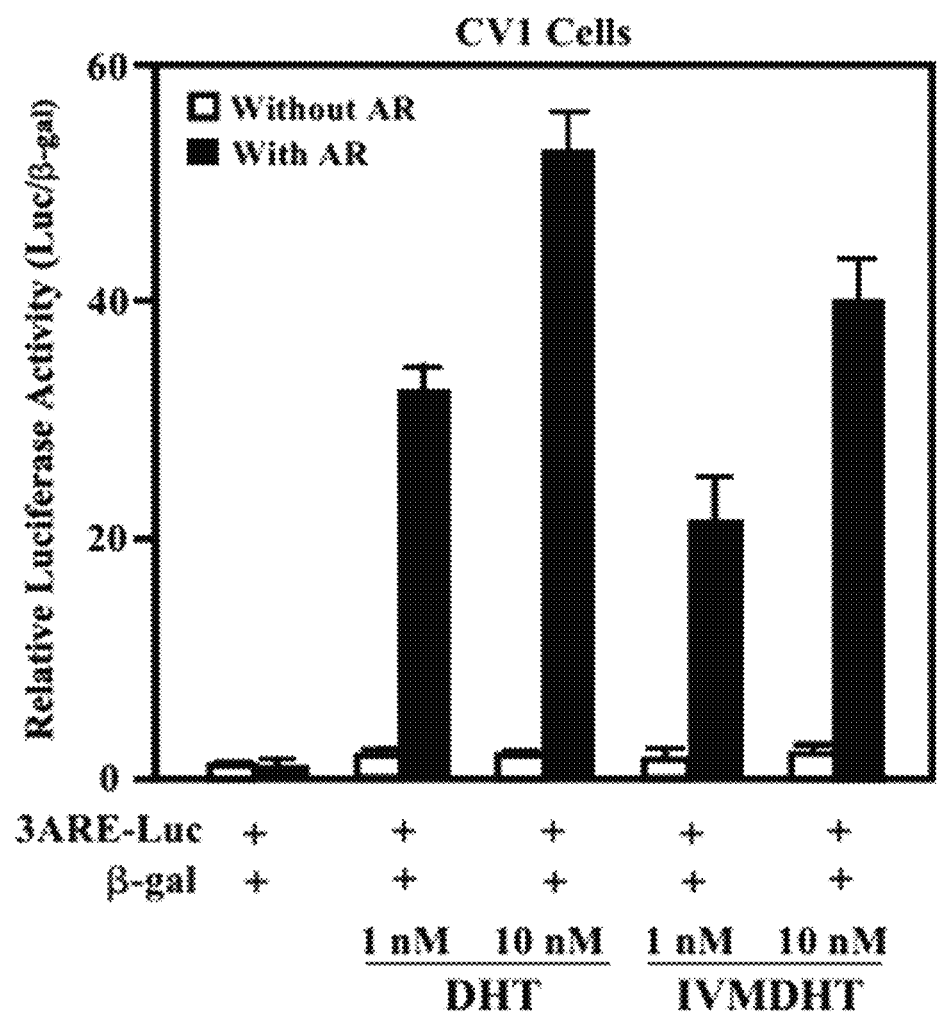
Figure 5E:
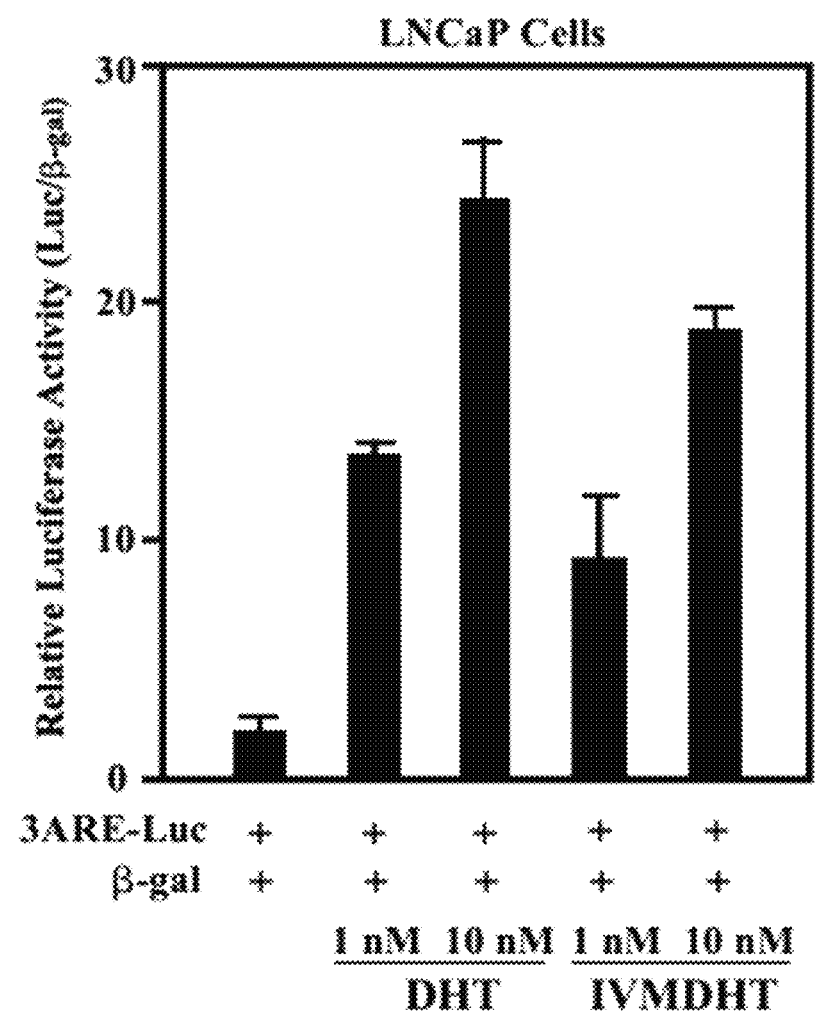

Determining the binding affinity and stability between radiolabeled DHT analogs and the AR. Experiments were performed to assess the biological activity of IVMDHT. It has been documented that androgens can induce the AR to translocate into the nucleus and to activate transcription through binding to androgen response elements (AREs) on the promoters of target genes Jenster et al, Mol Endocrinol, 5:1396-1404 (1991). IVMDHT was tested to see if it had similar activity as the parental DHT to translocate endogenous AR into the nucleus in LNCaP cells, an AR-positive human prostate cancer cell line. The AR protein is exclusively localized in the cytoplasm in the absence of androgens (FIG. 5A). Intriguingly, there was uniform nuclear staining of the AR protein in LNCaP cells cultured in the presence of IVMDHT, similar to that seen for DHT (FIG. 5B; FIG. 5C) indicating that IVMDHT translocated into the AR into the nucleus. To determine the activity of IVMDHT in activating AR-mediated transcription, CV1 (FIG. 5D) and LNCaP cells (FIG. 5E) were transfected with an androgen-inducible luciferase reporter vector driven by AREs together either with or without the human AR expression vector. An increase in AR-mediated luciferase activity was observed in the both CV1 and LNCaP cells in the presence of 1 nM and 10 nM IVMDHT, which is comparable to those with DHT.

This data demonstrate that IVMDHT crossed the cell membrane, similar to DHT, and induced AR nuclear translocation and transcriptional activity at physiological concentrations.

Example 4

To determine the specific binding affinity of IVMDHT with the AR in vivo, microPET imaging and biodistribution assays were performed. The binding specificity of $^{124}$IVMDHT in 4-month-old castrated and intact C57/B6 male mice (n=4 per group) was evaluated. All mice were given SSKI (saturated solution of potassium iodide; 20 μg/ml) in their water bottle 72 hours before they received 3.7 MBq of $^{124}$IVMDHT via intravenous injection through the tail vein. A series of microPET images were taken at 1, 2, and 6 hours from the intact and castrated mice (see representative images FIGS. 6A1-6A3 and FIGS. 6B1-6B3, respectively). Specific signals in the vicinity of the bladder/prostate was observed at 1 and 2 hours (arrows shown in FIGS. 6A1-6A2 and FIGS. 6B1-6B2) from both the intact and castrated mice.

Figure 1B:
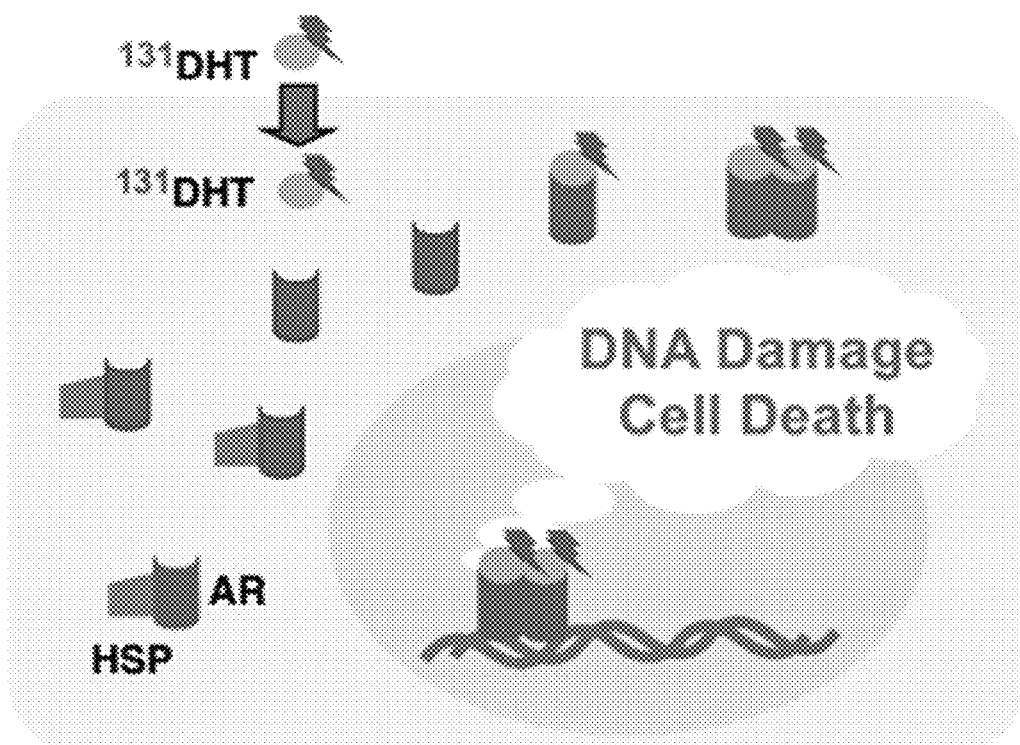
Figure 3C:
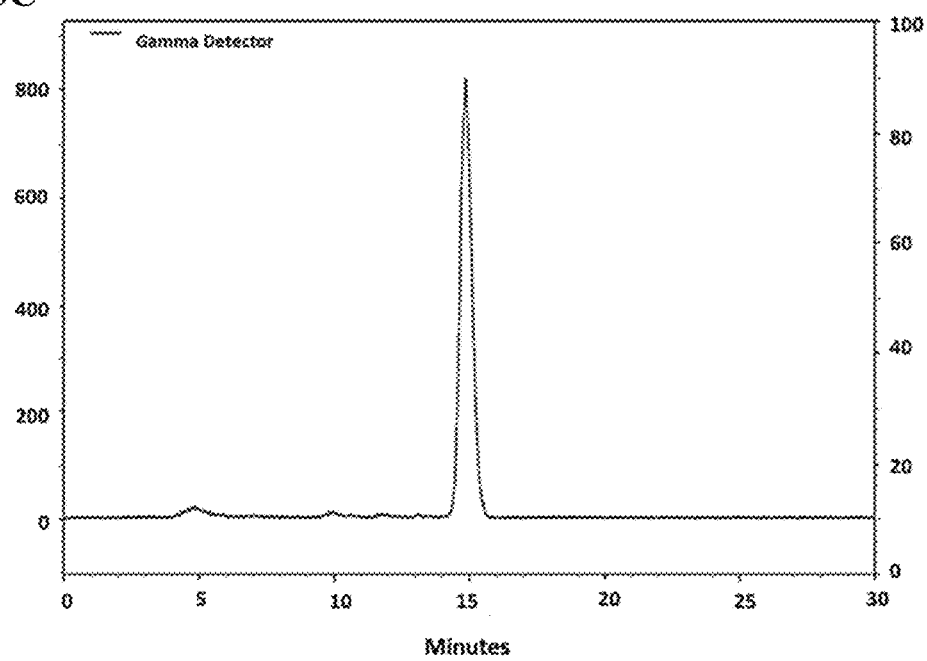
Figure 3D:
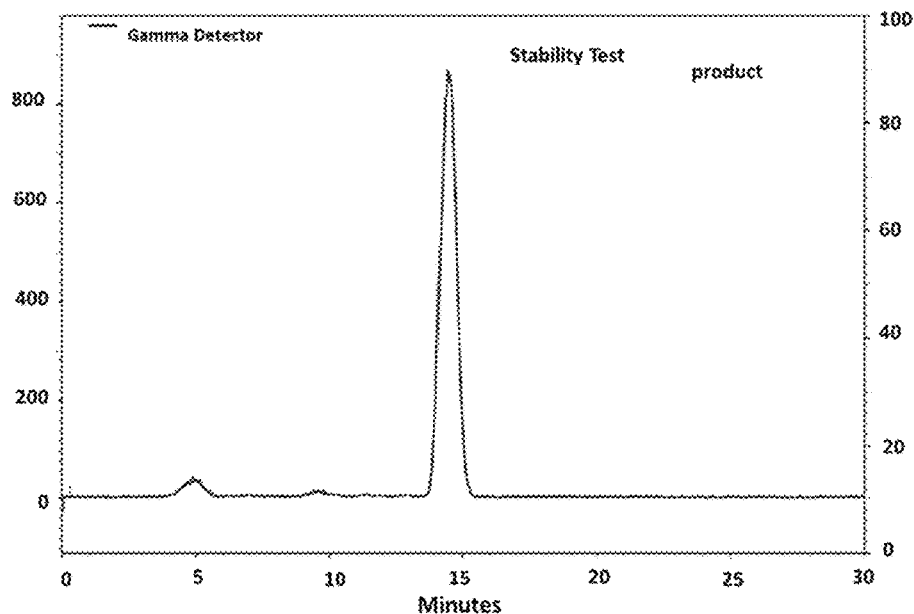
Figure 6A:
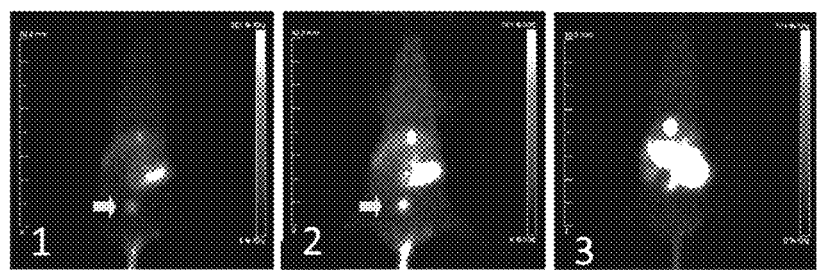
FIGS. 6A-6E. The androgen analog $^{124}$IVMDHT was intravenously injected into the tail-vein of intact (FIGS. 6A) and castrated mice (FIG. 6B) and imaged at 1 hour (FIG. 6A panel 1, FIG. 6B panel 1), 2 hours (FIG. 6A panel 2, FIG. 6B panel 2) and 6 hours (FIG. 6A panel 3, FIG. 6B panel 3). Localization of $^{124}$IVMDHT was seen in the vicinity of the prostate at 1 hour (arrows in FIG. 6A1, FIG. 6B panel 1), and 2 hours (arrows in FIG. 6A panel 2, FIG. 6B panel 2). $^{124}$IVNDHT was tested using similar approaches as described in FIG. 6A and FIG. 6B. Specific signals were observed at 1 hour (arrow in FIG. 6C panel 1) and 2 hours (arrow in FIG. 6C panel 2). $^{124}$IVMDHT was intraperitoneally injected into intact C57/B6 mice (FIG. 6D) and castrated C57/B6 mice (FIG. 6E). The mice were then analyzed at 1 hour (FIG. 6D panel 1, FIG. 6E panel 1), 2 hour (FIG. 6D panel 2, FIG. 6E panel 2) and 6 hours (FIG. 6D panel 3, FIG. 6E panel 3). Positive images are shown with arrows.
Figure 6B:
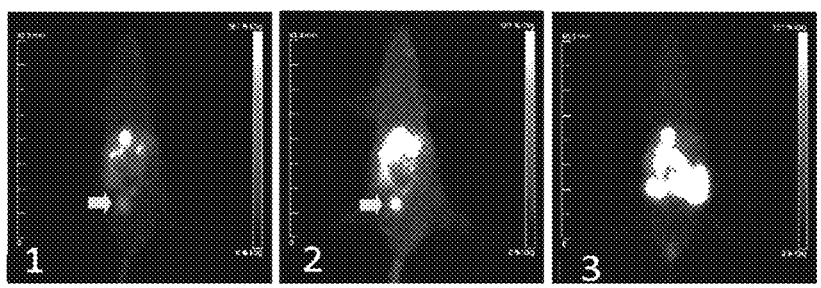
Figure 6C:
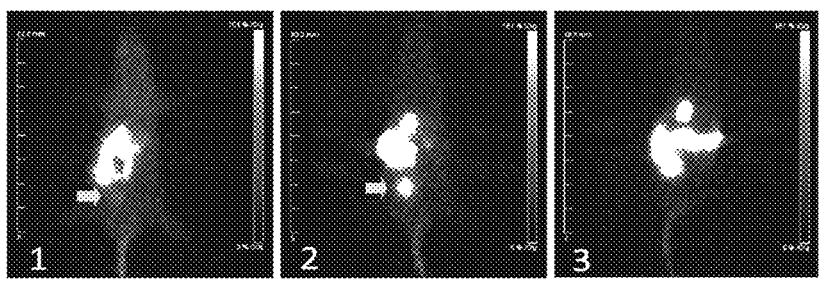
Figure 6D:
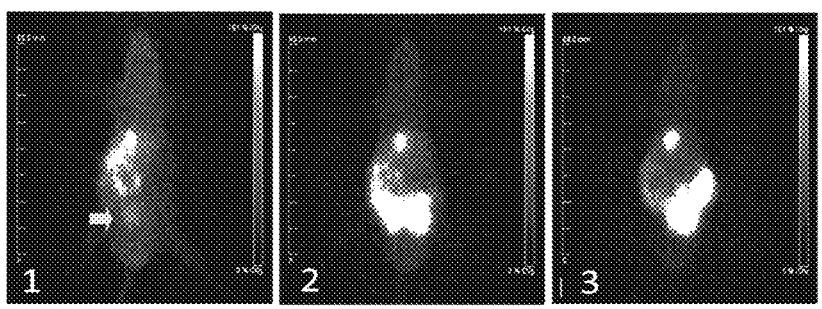
Figure 6E:
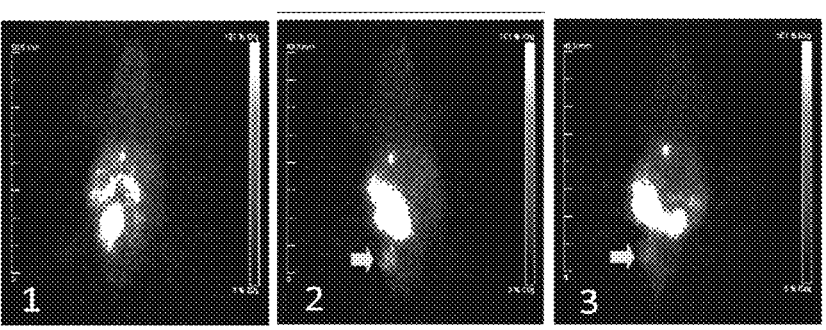

Using a similar experimental approach, IVMDHT was assessed in C57/B6 male mice. As shown in FIG. 6C1-6C3, specific signals were observed in mice injected with 3.7 MBq of $^{124}$IVNDHT. The intake rate of $^{124}$IVNDHT was further assessed by intraperitoneal injection. 1.2 MBq of $^{124}$IVNDHT was intraperitoneally injected into intact and castrated C57/B6 mice and microPET images were taken at 1, 2, and 6 hours. Specific signals were observed in the vicinity of the bladder/prostate at 2 and 6 hours in castrated mice (FIGS. 6E2-6E3).

The data indicates that low dosage and intraperitoneal injections extend the specific intake of IVMDHT.

Example 5

Figure 7:
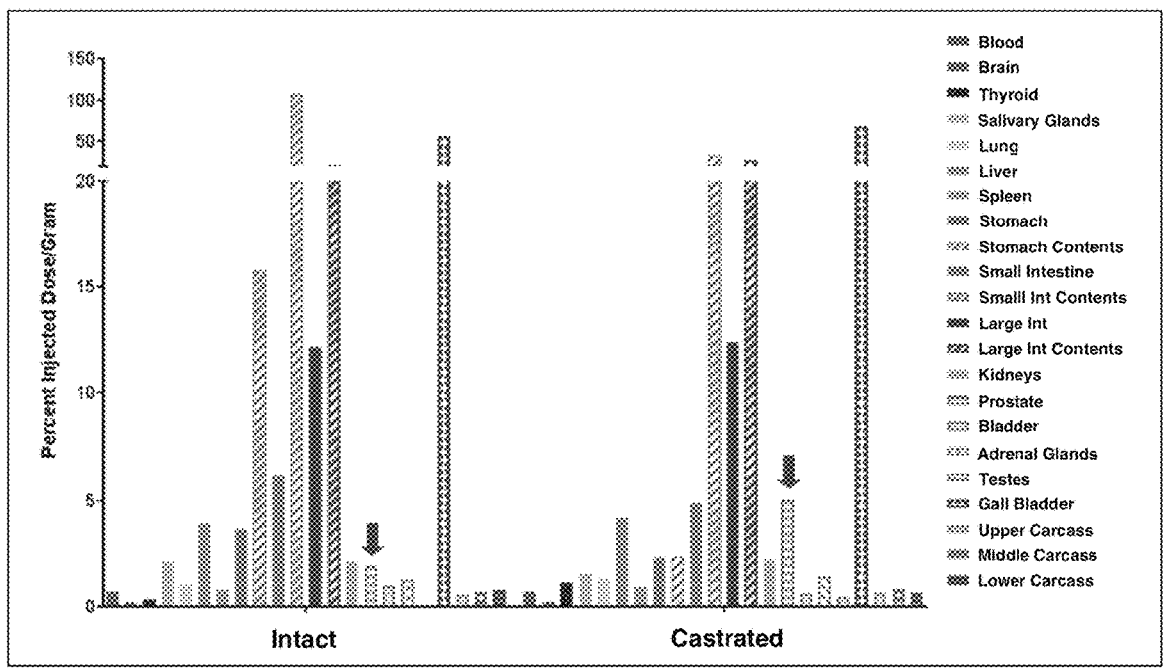
FIG. 7. Different mouse tissues were collected from either castrated or intact mice 6 hours after administrated with 3.7 MBq of $^{124}$IVMDHT. Specific intakes were measured as % ID/g and total counts per organ. The arrows indicate prostate tissue. From left to right in FIG. 7, the tissue are blood, brain, thyroid, salivary glands, lung, liver, spleen, stomach, stomach contents, small intestine, small intestine contents, large intestine, large intestine contents, kidneys, prostate, bladder, adrenal glands, testes, gall bladder, upper carcass, middle carcass, lower carcass (all for intact mice) and blood, brain, thyroid, salivary glands, lung, liver, spleen, stomach, stomach contents, small intestine, small intestine contents, large intestine, large intestine contents, kidneys, prostate, bladder, adrenal glands, testes, gall bladder, upper carcass, middle carcass, lower carcass (all for castrated mice).
Figure 8:
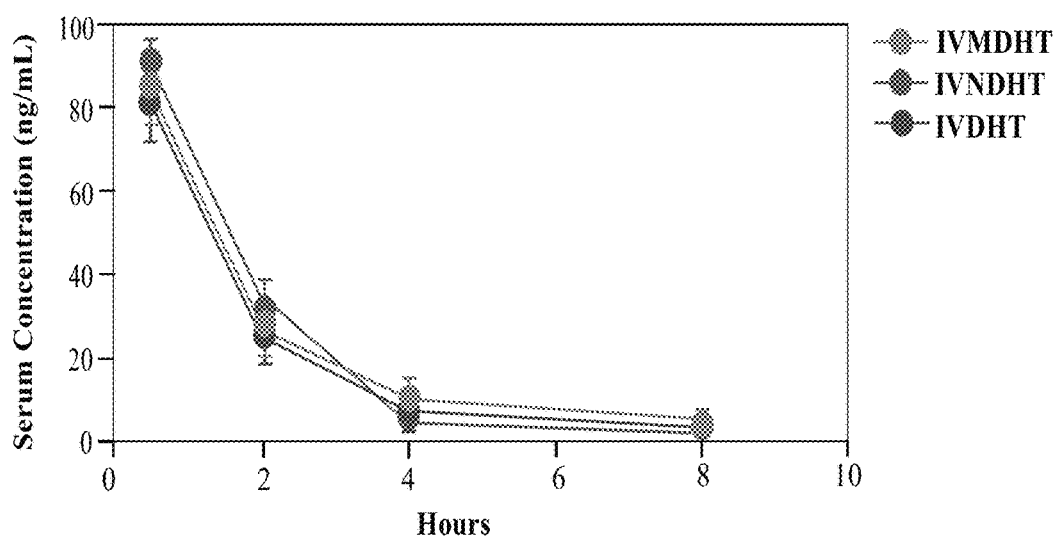
FIG. 8. C57B6 mice were intravenously injected with 50 μg of IVMDHT, IVNDHT, and IVDHT. Blood samples were collected at 1, 2, 4, and 8 hours (n=4) and the serum concentrations of the compounds were analyzed by liquid chromatography mass spectrometry. With reference to 2 hours on FIG. 8, the upper line represents IVMDHT; the middle line represents IVNDHT, and the lower line represents IVDHT.

Tissue biodistributions were assessed after the terminal scan with mice as shown in FIG. 7. Mouse tissue samples were weighed and counted and the results expressed as % ID/g and total counts per organ. Intriguingly, more intake of $^{124}$IVMDHT was observed in castrated mice than their intact counterparts (arrows shown in FIG. 7).

Example 6

To assess the stability of different androgen analogs, 50 μg of IVDHT, IVNDHT, and IVMDHT was intravenously injected into C57/B6 mice. Blood samples were collected from the mice at 1, 2, 4, and 8 hours and analyzed by liquid chromatography/mass spectrometry (n=4). As shown in FIG. 8, 40-60 ng/ml of three androgen analogs was shown in mice sera, indicating that the half-lives of these androgen analogs was about 1.5 hours. Taken together, the data demonstrates that androgen analogs have specific binding activity with the prostate of mice.

While preferred embodiments of the disclosures have been shown and described herein, it will be obvious to the skilled artisan that such embodiments are provided by way of example. Numerous variations will now occur to the skilled artisan without departing from the invention. It is intended that the following claims define the scope of the invention and that methods and structures within the scope of these claims and their equivalents be covered thereby.

What is claimed is:

1. A method of treating advanced prostate cancer in a subject in need thereof, the method comprising administering to the subject:
   (i) an effective amount of abiraterone; and
   (ii) an effective amount of a radionuclide-labeled 7α-(E-2'-iodovinyl)-17α-methyl-5α-dihydrotestosterone; wherein the radionuclide is iodine$^{-131}$;
to treat the advanced prostate cancer.

2. The method of claim 1, wherein the advanced prostate cancer is metastatic prostate cancer.

3. A method of treating advanced prostate cancer in a subject in need thereof, the method comprising administering to the subject:
   (i) an effective amount of abiraterone, abarelix, apalutamide, degarelix, goserelin, leuprorelin, or ozarelix; and
   (ii) an effective amount of a radionuclide-labeled 7α-(E-2'-iodovinyl)-5α-dihydrotestosterone, a radionuclide-labeled 7α-(E-2'-iodovinyl)-17α-methyl-5α-dihydrotestosterone, or a radionuclide-labeled 7α-(E-2'-iodovinyl)-19-nor-5α-dihydrotestosterone; wherein the radionuclide is iodine$^{-125}$, iodine$^{-131}$, or lutetium$^{-177}$;
to treat the advanced prostate cancer.

4. The method of claim 3, wherein (ii) comprises administering the radionuclide-labeled 7α-(E-2'-iodovinyl)-5α-dihydrotestosterone.

5. The method of claim 3, wherein (ii) comprises administering the radionuclide-labeled 7α-(E-2'-iodovinyl)-17α-methyl-5α-dihydrotestosterone.

6. The method of claim 3, wherein (ii) comprises administering the radionuclide-labeled 7α-(E-2'-iodovinyl)-19-nor-5α-dihydrotestosterone.

7. The method of claim 3, wherein the radionuclide is iodine$^{-125}$.

8. The method of claim 3, wherein the radionuclide is iodine$^{-131}$.

9. The method of claim 3, wherein the radionuclide is lutetium$^{-177}$.

10. The method of claim 3, wherein the advanced prostate cancer is metastatic prostate cancer.

11. A method of treating advanced prostate cancer in a subject in need thereof, the method comprising administering to the subject:
   (i) an effective amount of an anti-androgen compound; and
   (ii) an effective amount of radionuclide-labeled androgen wherein the radionuclide-labeled androgen is a radionuclide-labeled 7α-(E-2'-iodovinyl)-5αdihydrotestosterone, a radio-nuclide labeled 7α-(E-2'-iodovinyl-17α-methyl-5α-dihydrotestosterone, or a radio-nuclide labeled 7α-(E-2'-iodovinyl)-19-nor-5α-dihydrotestosterone,
to treat the advanced prostate cancer.

12. The method of claim 11, wherein the advanced prostate cancer is Stage III prostate cancer.

13. The method of claim 11, wherein the advanced prostate cancer is Stage IV prostate cancer.

14. The method of claim 11, wherein the advanced prostate cancer is metastatic prostate cancer.

15. The method of claim 11, wherein the anti-androgen compound is a gonadotropin-releasing hormone antagonist, a gonadotropin-releasing hormone agonist, a luteinizing hormone-releasing hormone agonist, or a luteinizing hormone-releasing hormone antagonist.

16. The method of claim 11, wherein the anti-androgen compound is abarelix, abiraterone, apalutamide, degarelix, goserelin, leuprorelin, or ozarelix.

17. The method of claim 11, wherein the radionuclide-labeled androgen is a radionuclide-labeled testosterone, a radionuclide-labeled testosterone analog, a radionuclide-labeled dihydrotestosterone, or a radionuclide-labeled dihydrotestosterone analog.

18. The method of claim 11, wherein the radionuclide is bismuth$^{-213}$, caesium$^{-131}$, caesium$^{-137}$, chromium$^{-51}$, cobalt$^{-57}$, cobalt$^{-60}$, copper$^{-64}$, copper$^{-67}$, dysprosium$^{-165}$, erbium$^{-169}$, fluorine$^{-18}$, gallium$^{-67}$, gallium$^{-68}$, germanium$^{-68}$, holmium$^{-166}$, indium$^{-111}$, iodine$^{-123}$, iodine$^{-124}$, iodine$^{-125}$, iodine$^{-131}$, iridium$^{-192}$, iron$^{-59}$, krypton$^{-81m}$, lead$^{-212}$, lutetium$^{-177}$, molybdenum$^{-99}$, palladium$^{-103}$, phosphorus$^{-32}$, potassium$^{-42}$, radium$^{-223}$, rhenium$^{-186}$, rhenium$^{-188}$, rubidium$^{-81}$, rubidium$^{-82}$, samarium$^{-153}$, selenium$^{-75}$, sodium$^{-24}$, strontium$^{-82}$, strontium$^{-89}$, technetium$^{-99m}$, thallium$^{-201}$, xenon$^{-133}$, ytterbium$^{-169}$, ytterbium$^{-177}$, or yttrium$^{-90}$.

19. A compound selected from the group consisting of radionuclide-labeled 7α-(E-2'-iodovinyl)-5α-dihydrotestosterone; radionuclide-labeled 7α-(E-2'-iodovinyl)-17α-methyl-5α-dihydrotestosterone; and radionuclide-labeled 7α-(E-2'-iodovinyl)-19-nor-5α-dihydrotestosterone; wherein the radionuclide is iodine$^{-123}$, iodine$^{-124}$, iodine$^{-125}$, iodine$^{-131}$, or lutetium$^{-177}$.

20. The compound of claim 19, wherein the radionuclide is iodine$^{-123}$.

21. The compound of claim 19, wherein the radionuclide is iodine$^{-124}$.

22. The compound of claim 19, wherein the radionuclide is iodine$^{-125}$.

23. The compound of claim 19, wherein the radionuclide is iodine$^{-131}$.

24. The compound of claim 19, wherein the radionuclide is lutetium$^{-177}$.

25. A pharmaceutical composition comprising the compound of claim 19 and a pharmaceutically acceptable carrier.

26. A compound selected from the group consisting of:

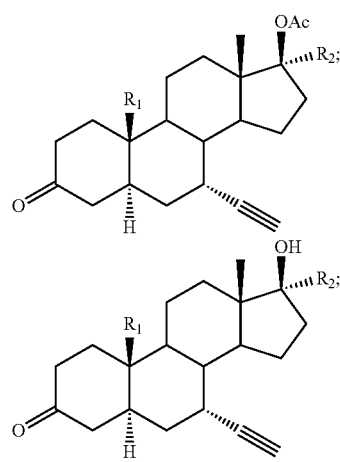

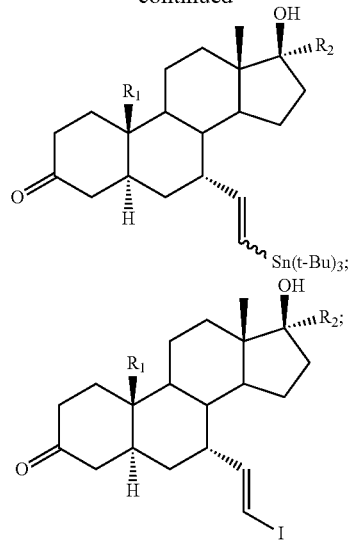

wherein $R_1$ and $R_2$ are H; wherein $R_1$ and $R_2$ are methyl; or wherein $R_1$ is methyl and $R_2$ is H; and
wherein I is iodine$^{-123}$, iodine$^{-124}$, iodine$^{-125}$, or iodine$^{-131}$.

27. A method of treating advanced prostate cancer in a subject in need thereof, the method comprising administering to the subject an effective amount of the compound of claim 19.

28. The method of claim 27, further comprising administering to the patient an effective amount of an anti-androgen compound.

29. The method of claim 28, wherein the anti-androgen compound is a gonadotropin-releasing hormone antagonist, a gonadotropin-releasing hormone agonist, a luteinizing hormone-releasing hormone agonist, or a luteinizing hormone-releasing hormone antagonist.

30. The method of claim 28, wherein the anti-androgen compound is abiraterone, apalutamide, degarelix, goserelin, leuprorelin, or ozarelix.

31. The method of claim 27, wherein the subject has undergone surgical orchiectomy prior to treatment with the radionuclide-labeled androgen.

32. The method of claim 27, wherein the advanced prostate cancer is metastatic prostate cancer or metastatic castration-resistant prostate cancer.

33. The method of claim 1, wherein abiraterone is administered to the subject prior to the radionuclide-labeled 7α-(E-2'-iodovinyl)-17α-methyl-5α-dihydrotestosterone.

34. The method of claim 3, wherein abiraterone, abarelix, apalutamide, bicalutamide, degarelix, goserelin, leuprorelin, nilutamide, or ozarelix is administered to the subject prior to the radionuclide-labeled 7α-(E-2'-iodovinyl)-5α-dihydrotestosterone, the radionuclide-labeled 7α-(E-2'-iodovinyl)-17α-methyl-5α-dihydrotestosterone, or the radionuclide-labeled 7α-(E-2'-iodovinyl)-19-nor-5α-dihydrotestosterone.

35. The method of claim 11, wherein the anti-androgen compound is administered to the subject prior to the radionuclide-labeled androgen or the analog thereof.

* * * * *